US012427094B2

(12) United States Patent
Harris et al.

(10) Patent No.: US 12,427,094 B2
(45) Date of Patent: Sep. 30, 2025

(54) ENTERAL FEEDING BAG AND PUMP SUPPORT

(71) Applicant: KPR U.S., LLC, Mansfield, MA (US)

(72) Inventors: Benjamin Harris, Plainville, MA (US); Joel Wiesner, O'Fallon, MO (US); Jeffrey Markwardt, Maryland Heights, MO (US); Wayne Biermann, St. Charles, MO (US); Kenneth Breitweiser, Brighton, IL (US)

(73) Assignee: KPR U.S., LLC, Mansfield, MA (US)

( * ) Notice: Subject to any disclaimer, the term of this patent is extended or adjusted under 35 U.S.C. 154(b) by 15 days.

(21) Appl. No.: 15/084,694

(22) Filed: Mar. 30, 2016

(65) Prior Publication Data
US 2016/0317392 A1 Nov. 3, 2016

Related U.S. Application Data

(60) Provisional application No. 62/140,133, filed on Mar. 30, 2015, provisional application No. 62/139,954, filed on Mar. 30, 2015.

(51) Int. Cl.
*A45F 3/04* (2006.01)
*A61J 1/10* (2006.01)
(Continued)

(52) U.S. Cl.
CPC ............. *A61J 15/0026* (2013.01); *A45F 3/04* (2013.01); *A61J 1/10* (2013.01); *A61J 1/12* (2013.01);
(Continued)

(58) Field of Classification Search
CPC .............. A61M 5/1415; A61M 5/1414; F16M 2200/024
(Continued)

(56) References Cited

U.S. PATENT DOCUMENTS 4,759,749 A * 7/1988 Verkaart ................. A61M 5/44
165/156
4,832,299 A * 5/1989 Gorton ..................... A61G 7/05
248/231.71
(Continued)

FOREIGN PATENT DOCUMENTS

WO 2004082560 A1 9/2004
WO 2015010060 A1 1/2015

OTHER PUBLICATIONS

International Search Report dated Feb. 3, 2017 in related International Application No. PCT/US2016/024900, 7 pages.
(Continued)

Primary Examiner — Scott T McNurlen
(74) Attorney, Agent, or Firm — ArentFox Schiff LLP

(57) ABSTRACT

An enteral feeding bag support system for use in a medical environment to suspend a medical bag above a surface includes a base including a support portion for supporting the support on the support surface, and an attachment portion for removably attaching a medical device to the support. A pole assembly includes a medical bag attachment portion for attaching a medical bag to the pole assembly. The pole assembly is attachable to the base such that when the pole assembly is attached to the base and the base is on the support surface, the pole assembly extends from the base so that the medical bag attachment portion is disposed above the base suspending the medical bag above the support surface.

13 Claims, 38 Drawing Sheets

(51) Int. Cl.
*A61J 1/12* (2006.01)
*A61J 15/00* (2006.01)
*A61M 5/14* (2006.01)
*F16M 11/04* (2006.01)
*F16M 11/24* (2006.01)
*A45F 3/00* (2006.01)
*F16M 11/10* (2006.01)

(52) U.S. Cl.
CPC .......... *A61J 15/003* (2013.01); *A61M 5/1415* (2013.01); *F16M 11/041* (2013.01); *F16M 11/046* (2013.01); *F16M 11/242* (2013.01); *A45F 2003/003* (2013.01); *F16M 11/10* (2013.01); *F16M 2200/024* (2013.01); *F16M 2200/027* (2013.01); *F16M 2200/08* (2013.01)

(58) Field of Classification Search
USPC ................ D24/128; 248/188.7, 188.1, 188.8
See application file for complete search history.

(56) References Cited

U.S. PATENT DOCUMENTS

| | | | | | |
|---|---|---|---|---|---|
| D306,076 | S | * | 2/1990 | Wood | D24/128 |
| 5,082,221 | A | * | 1/1992 | Lai | F16M 11/242 248/168 |
| D331,108 | S | * | 11/1992 | Curbbun | D24/128 |
| 5,794,913 | A | * | 8/1998 | Ho | F16M 11/22 248/615 |
| 6,311,941 | B1 | * | 11/2001 | Feldmeyer | A47B 97/00 248/188.8 |
| 6,431,505 | B2 | * | 8/2002 | Chinn | A61M 5/1415 248/121 |
| 6,695,268 | B1 | * | 2/2004 | Hsieh | A47B 19/002 248/188.7 |
| 8,567,730 | B1 | * | 10/2013 | Stevenson | A61M 5/1415 248/125.8 |
| 8,695,957 | B2 | * | 4/2014 | Quintania | B25B 5/006 248/309.1 |
| 2002/0088834 | A1 | * | 7/2002 | Wolfgram | A45F 3/04 224/629 |
| 2005/0040126 | A1 | | 2/2005 | Gaster | |
| 2005/0269464 | A1 | * | 12/2005 | Adelman | A61M 5/1414 248/170 |
| 2008/0116157 | A1 | * | 5/2008 | Fulbrook | A61M 5/1415 211/60.1 |
| 2008/0135713 | A1 | * | 6/2008 | Santoro | A47B 97/04 248/346.03 |
| 2010/0282807 | A1 | * | 11/2010 | Sisk | A45F 3/02 224/602 |
| 2013/0075438 | A1 | * | 3/2013 | Christy | A45F 3/042 224/644 |

OTHER PUBLICATIONS

Written Opinion of the International Searching Authority dated Feb. 3, 2017 in related International Application No. PCT/US2016/024900, 9 pages.

Examiner's Report dated Jan. 10, 2017 in related Canadian Application No. 170774, 2 pages.

* cited by examiner

ENTERAL FEEDING BAG AND PUMP SUPPORT

CROSS-REFERENCE TO RELATED APPLICATION

This application is a non-provisional of U.S. Patent Application Ser. No. 62/139,954 filed Mar. 30, 2015 and a non-provisional of U.S. Patent Application Ser. No. 62/140,133 filed Mar. 30, 2015, which is hereby incorporated by reference in its entirety.

TECHNICAL FIELD

This invention relates to a support for a medical bag. More particularly, the invention relates to a support for an enteral feeding bag that includes a medical device mounting assembly.

BACKGROUND

Medical bags such as IV/enteral feeding bags are typically suspended from an IV pole, tabletop bag hangers, or straps within a backpack. Medical devices such as enteral feeding pumps are typically attached to a support structure such as an IV pole, a bed rail, or other support structure by means of a pole clamp or other attachment device that holds the pump in a fixed position relative to the support structure. During medical treatment, such as enteral feeding, it can be difficult to position the IV pole and medical bag in close proximity to the medical device. As a result, the configuration of the medical bag and medical device support structures of the prior art can cause use of the devices to be cumbersome, and may severely restrict the patient's mobility or be unsuitable for bedside use.

SUMMARY

One or more aspects of the disclosure can be directed to an IV or an enteral feeding bag support for use in a medical environment to suspend a medical bag above a support surface. The enteral feeding bag support can comprise a base comprising a support portion for supporting the support on the support surface and an attachment portion for removably attaching a medical device to the support. A pole assembly can comprise a medical bag attachment portion for attaching a medical bag to the pole assembly. The pole assembly may be attachable to the base such that when the pole assembly is attached to the base and the base is on the support surface, the pole assembly extends from the base so that the medical bag attachment portion is disposed above the base suspending the medical bag above the support surface.

The support portion can comprise at least one foot attached to the base for engaging the support surface. The foot may be movably attached to the support portion for movement between a deployed position and a stowed position. The foot may be pivotably attached to the support portion for pivoting between the deployed and stowed positions. The foot may be slidably attached to the support portion for translational movement between the deployed and stowed positions. The foot may be releasably lockable in incremental positions between the stowed and deployed positions. The pole assembly can comprise a first elongate member and a second elongate member telescopingly received in the first elongate member for adjusting a relative position of the first and second elongate members. The second elongate member can comprise a first straight section for receipt in the first elongate member and a second curved section extending from the first straight section for attaching the medical bag. A lock may secure the second elongate member at a selected position relative to the first elongate member. The enteral feeding bag support may further comprise a medical device mounting assembly. The attachment portion can mount the medical device mounting assembly to the base. The support portion and the attachment portion can be formed as one piece of material. The enteral feeding bag support may be combined with a backpack. The base of the support can have a first configuration for supporting the medical bag on the support surface and a second configuration for supporting the medical bag in the backpack.

One or more further aspects of the disclosure can be directed to an enteral feeding bag support for use in a medical environment to suspend a medical bag above a support surface. The enteral feeding bag support can comprise a base comprising a support portion for supporting the support on the support surface and an attachment portion. A medical device mounting assembly may be movably attached to the attachment portion of the base to attach a medical device to the base. A pole assembly can comprise a medical bag attachment portion for attaching a medical bag to the pole assembly. The pole assembly may be mountable on the base such that when the pole assembly is mounted on the base and the base is on the support surface, the medical bag attachment portion is disposed above the base suspending the medical bag above the support surface.

The support portion and the attachment portion may be formed as one piece of material. The support portion can comprise at least one foot attached to the support portion for engaging the support surface. The support portion can comprise feet attached to the support portion for engaging the support surface. The feet may be selectively movable with respect to the base between a stowed position and a deployed position. The feet may be attached to the support portion for incremental movement from the stowed position to the deployed position. The enteral feeding bag support can be combined with a backpack. The base of the support may have a first configuration for supporting the medical bag on the support surface and a second configuration for supporting the medical bag in the backpack. The base may have padding at a back of the base for engaging a wearer of the backpack when the support is in the backpack.

There is further disclosed a combination backpack and medical fluid bag support, comprising a medical fluid bag support comprising a base assembly having at least one selectively adjustable foot, and means for attaching a medical device to the base assembly, a pole assembly coupled to the base assembly, the pole assembly having a medical fluid bag attachment portion configured to support the feeding bag thereunto and a means for disposing the pole bag attachment portion at at least one predetermined head height above said means for attaching the medical device; and a backpack portion configured to be supported on a wearer's shoulder and defining an internal storage compartment sized to receive therein the medical fluid bag support. The base assembly can have a plurality of independently adjustable feet, each of the independently adjustable feet having a stowed position and a plurality of selectively lockable deployed positions, and wherein the internal storage compartment is sized to receive therein the medical fluid support when each of the independently adjustable feet is in the stowed position. In some configurations, the at least one predetermined head height includes a first predetermined head height selectable when the medical fluid bag support is disposed in the internal storage compartment and a second predetermined head height selectable when the at least one selectively adjustable foot is engaged with the surface.

BRIEF DESCRIPTION OF THE DRAWINGS

Corresponding reference characters indicate corresponding parts throughout the several views of the drawings.

DETAILED DESCRIPTION

Figure 1:
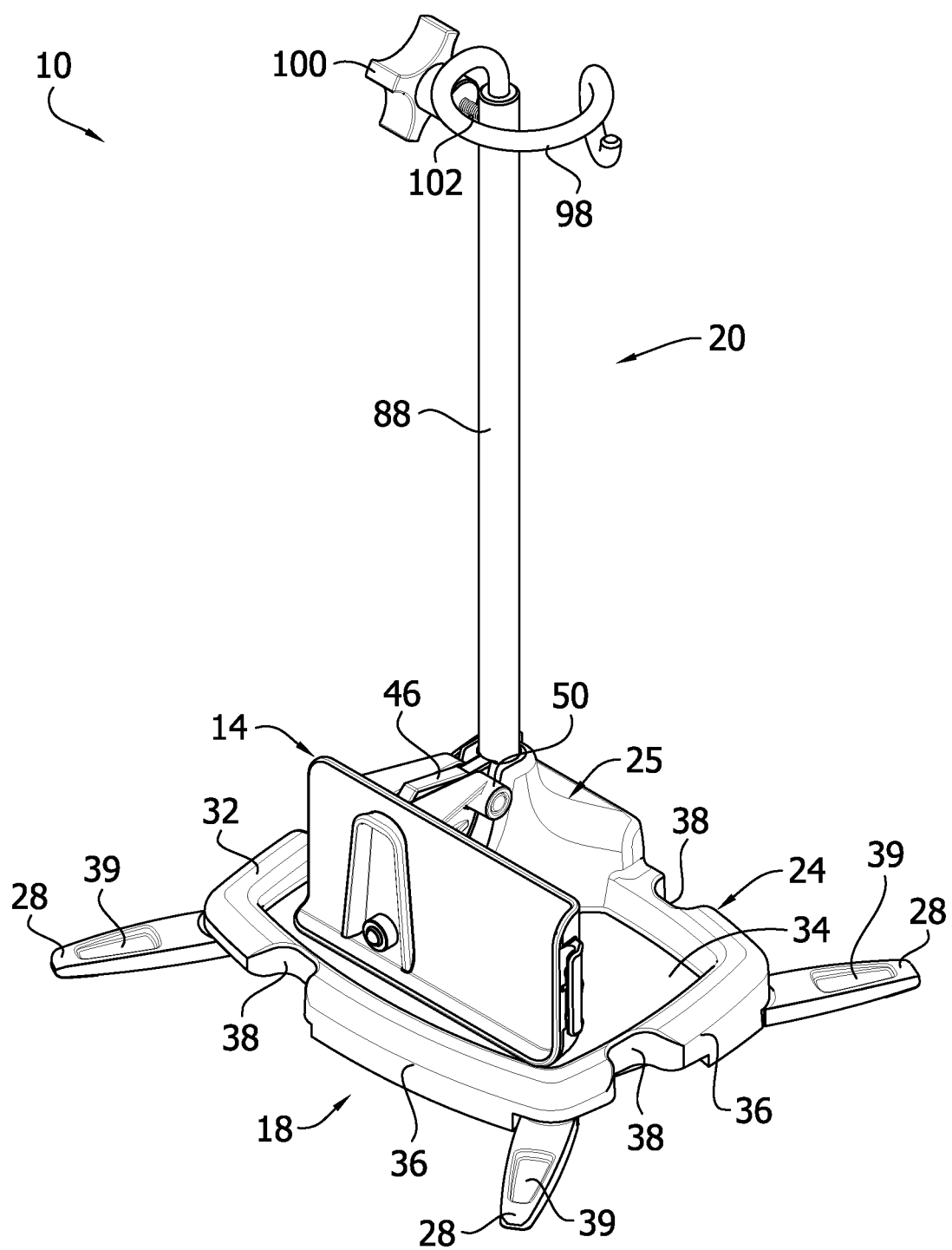
FIG. 1 is a perspective view of a enteral feeding bag support with feet shown in a deployed position.
Figure 9:
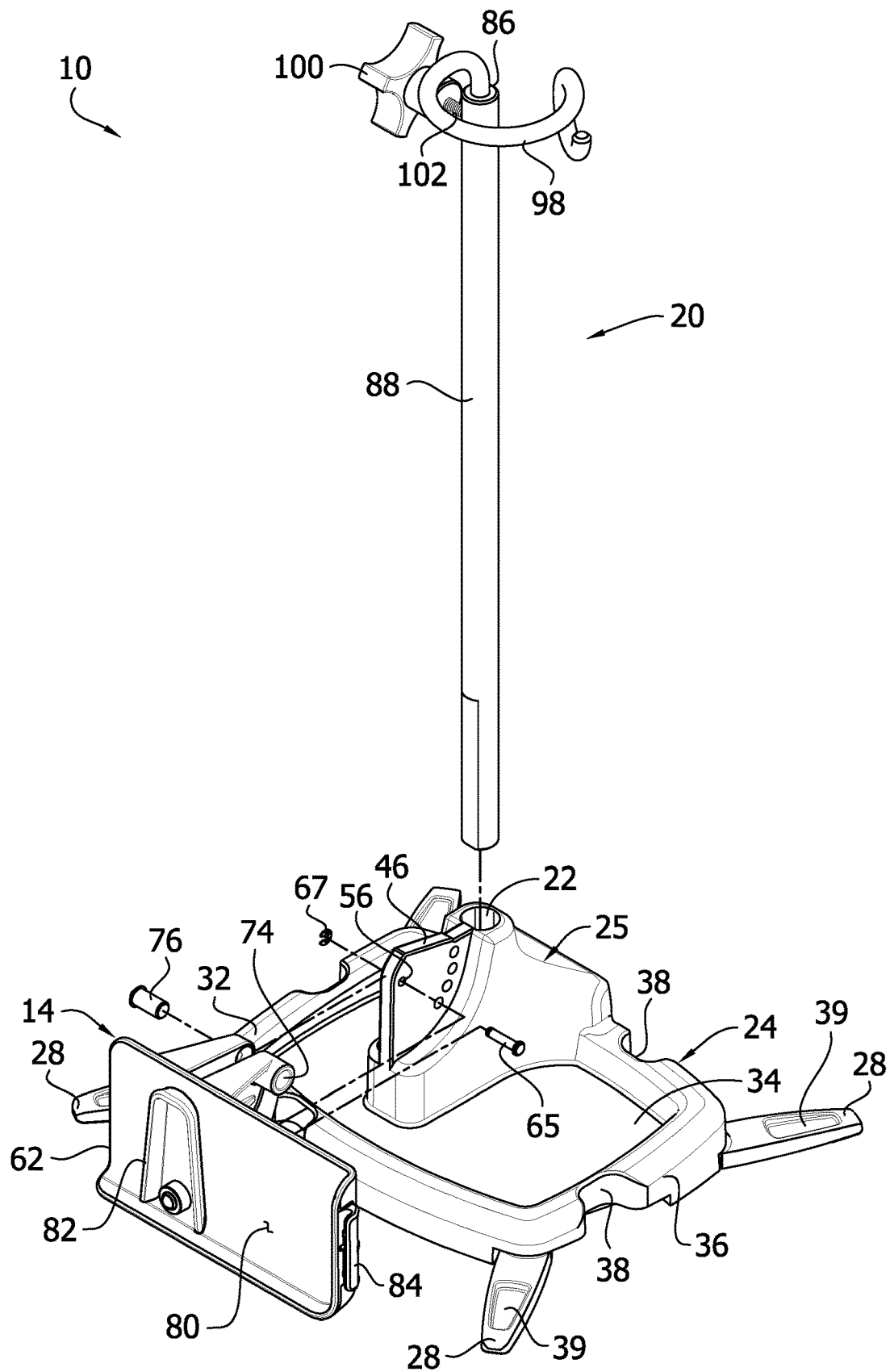
FIG. 9 is an exploded view of the support.

Referring to FIGS. 1 and 9, a enteral feeding bag support indicated generally at 10 may be used to suspend a medical bag 12 (FIG. 14), such as an IV or enteral feeding bag, above a support surface, such as a table. The support 10 may also be inserted into a backpack BP to suspend the medical bag in the backpack as shown in FIG. 14, e.g., in an internal compartment thereof. The support 10 may movably attach a medical device mounting assembly 14 for movably and releasably attaching a medical device such as a pump 16 (FIGS. 13 and 14) to the support to locate the pump below the medical bag 12 to deliver liquid from the medical bag to a patient.

Figure 10:
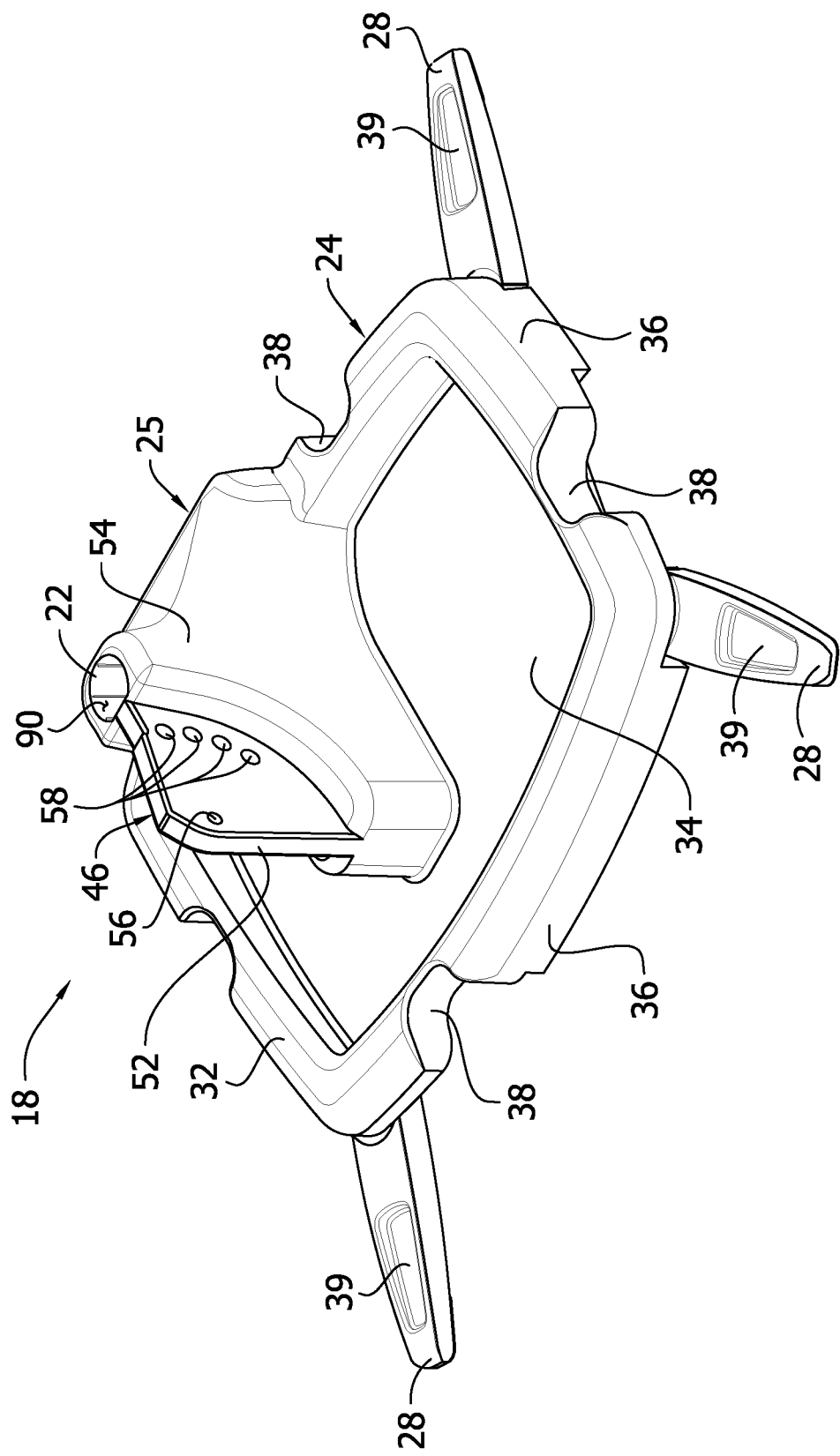
FIG. 10 is a front and right side perspective of a base of the support.
Figure 11:
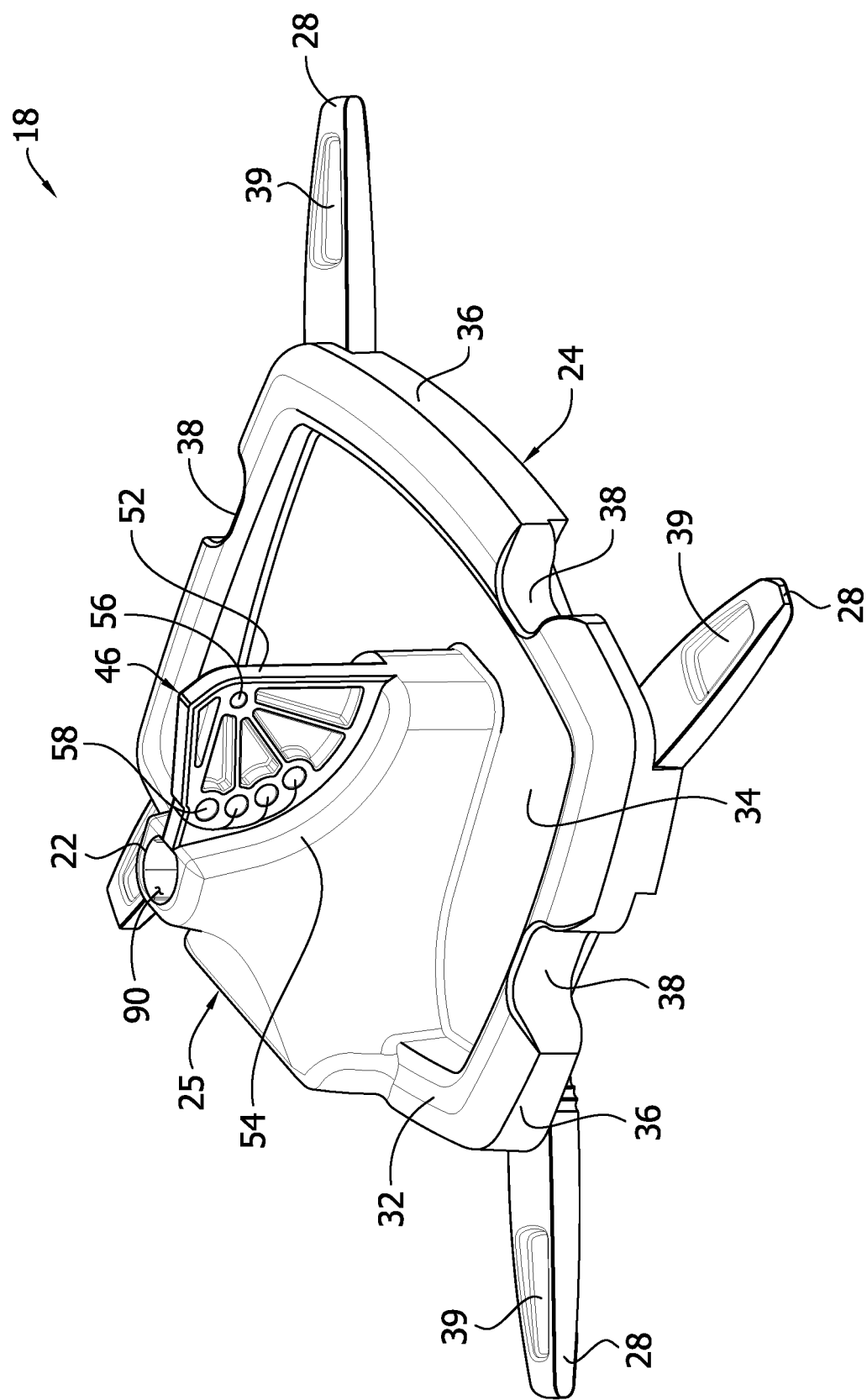
FIG. 11 is a front and left side perspective of the base of the support.

The enteral feeding bag support 10 may comprise a base 18 for supporting the support on the support surface, and a pole assembly 20 configured for attachment to the base to suspend the medical bag 12 above the support surface. The pole assembly 20 may be attached to the base 18 by inserting the pole assembly into an opening 22 (FIGS. 10 and 11) in the base and securing the pole assembly in the opening. It is envisioned that the pole assembly 20 can be secured to the base 18 is other ways without departing from the scope of the disclosure. Suitable structure (not shown) may be provided to secure the pole assembly 20 to the base 18 and/or to secure the pole assembly against rotation relative to the base.

Figure 7:
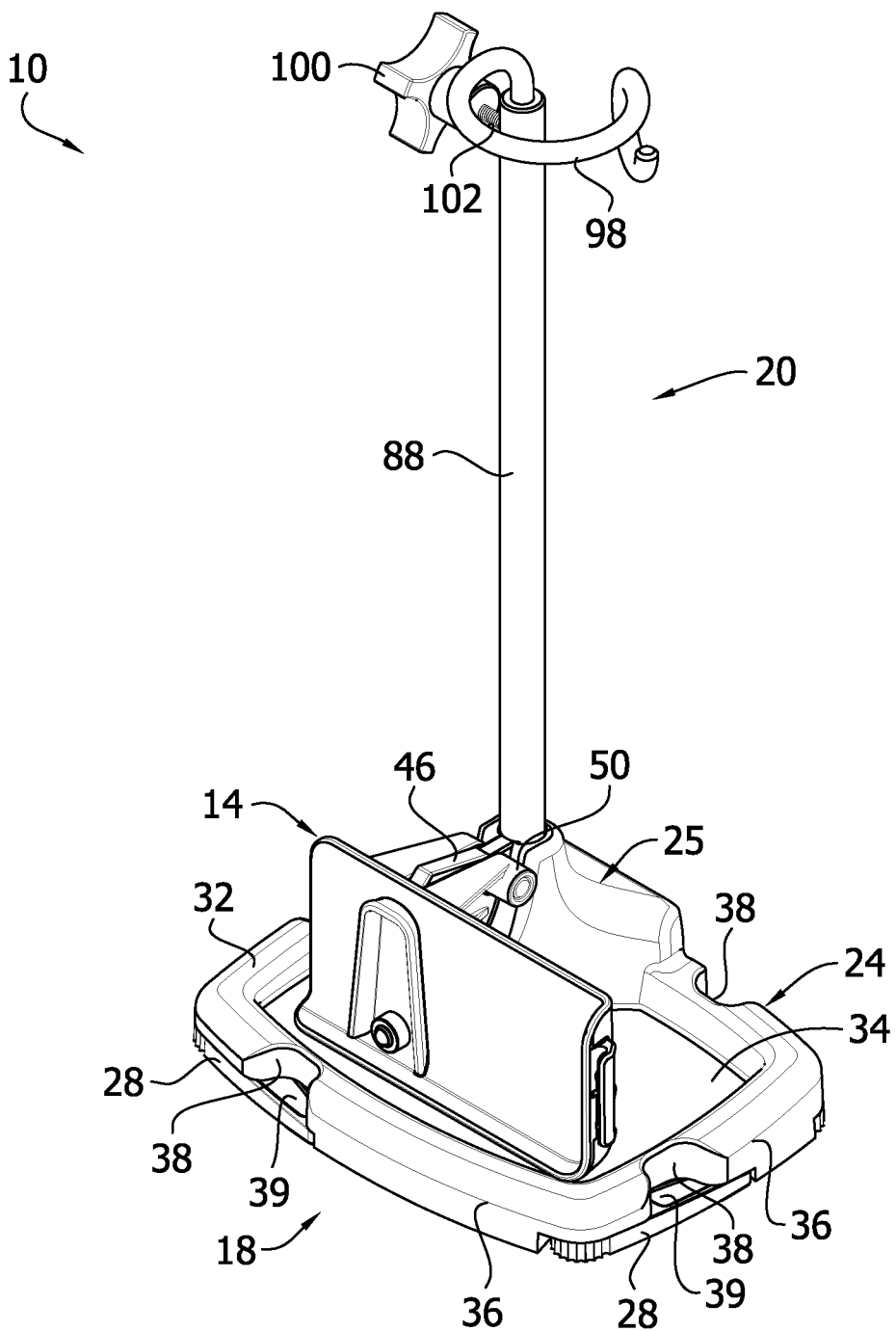
FIG. 7 is a perspective of the support with feet shown in a stowed position.
Figure 8:
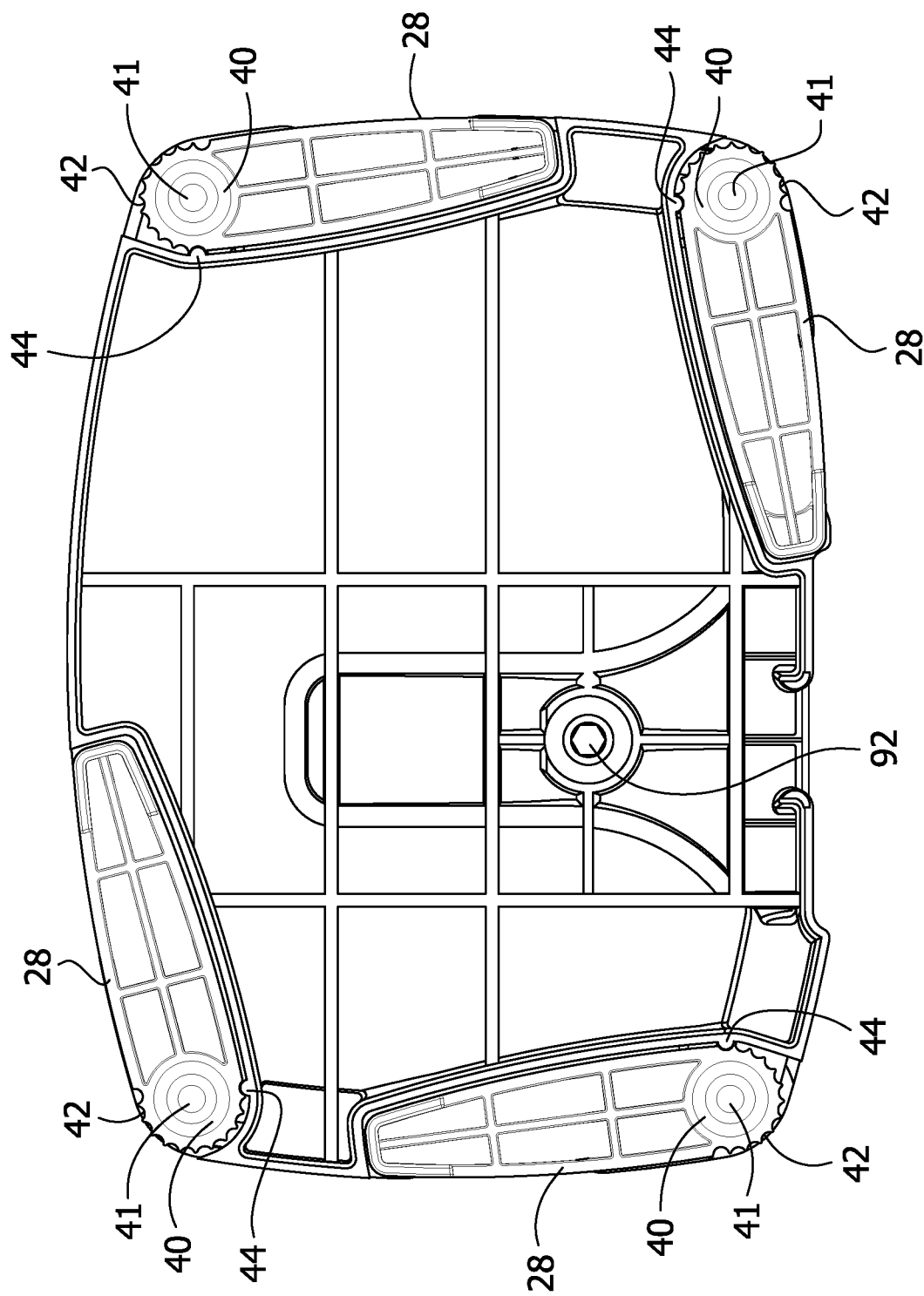
FIG. 8 is a bottom view of the support of FIG. 7.

Referring to FIGS. 1-8, the base 18 may comprise a support portion 24 for supporting the support 10 on the support surface and an attachment portion 25 for attaching the pole assembly 20 to the base and movably attaching the medical device mounting assembly 14 to the base. Feet 28 may be attached to a bottom of the support portion 24 for engaging the support surface to stabilize the support 10 on the support surface. In the illustrated embodiment, each foot 28 is pivotably attached to the bottom of the support portion 24 and movable between a deployed position (FIG. 1) and a stowed position (FIGS. 7 and 8). In the stowed position, the feet 28 may be received in pockets 30 in the bottom of the support portion 24 such that the feet are substantially within an outer perimeter of the support portion. In the deployed position the feet 28 may extend outward past the outer perimeter of the support portion 24 to provide a wider support base for the support 10. The feet 28 could be fixedly attached to the support portion 24 without departing from the scope of the disclosure. In the illustrated embodiment, there are four feet 28 attached to the support portion 24. However, any number of feet is envisioned.

The support portion 24 may have a rim 32 and a floor 34 recessed from the rim. The rim 32 and floor 34 define a tray of the support portion 24 which can be used to hold items associated with the use of the support 10. The rim 32 may have other constructions without departing from the scope of the disclosure. Sides 36 of the support portion 24 may have cutouts 38. In the illustrated embodiment, one cutout 38 is associated with each side 36. A portion of each cutout 38 may be aligned with at least a portion of a respective foot 28 when the foot is in the stowed position. The cutouts 38 provide access to the feet 28 from a side and/or from above the support portion 24 so that the feet can be grasped and moved to the deployed position when the support 10 is supported on a support surface. A recessed portion 39 in a top of each foot 28 may provide an area to grip the foot to facilitate grasping the foot and moving it from the stowed position to the deployed position.

Figure 3:
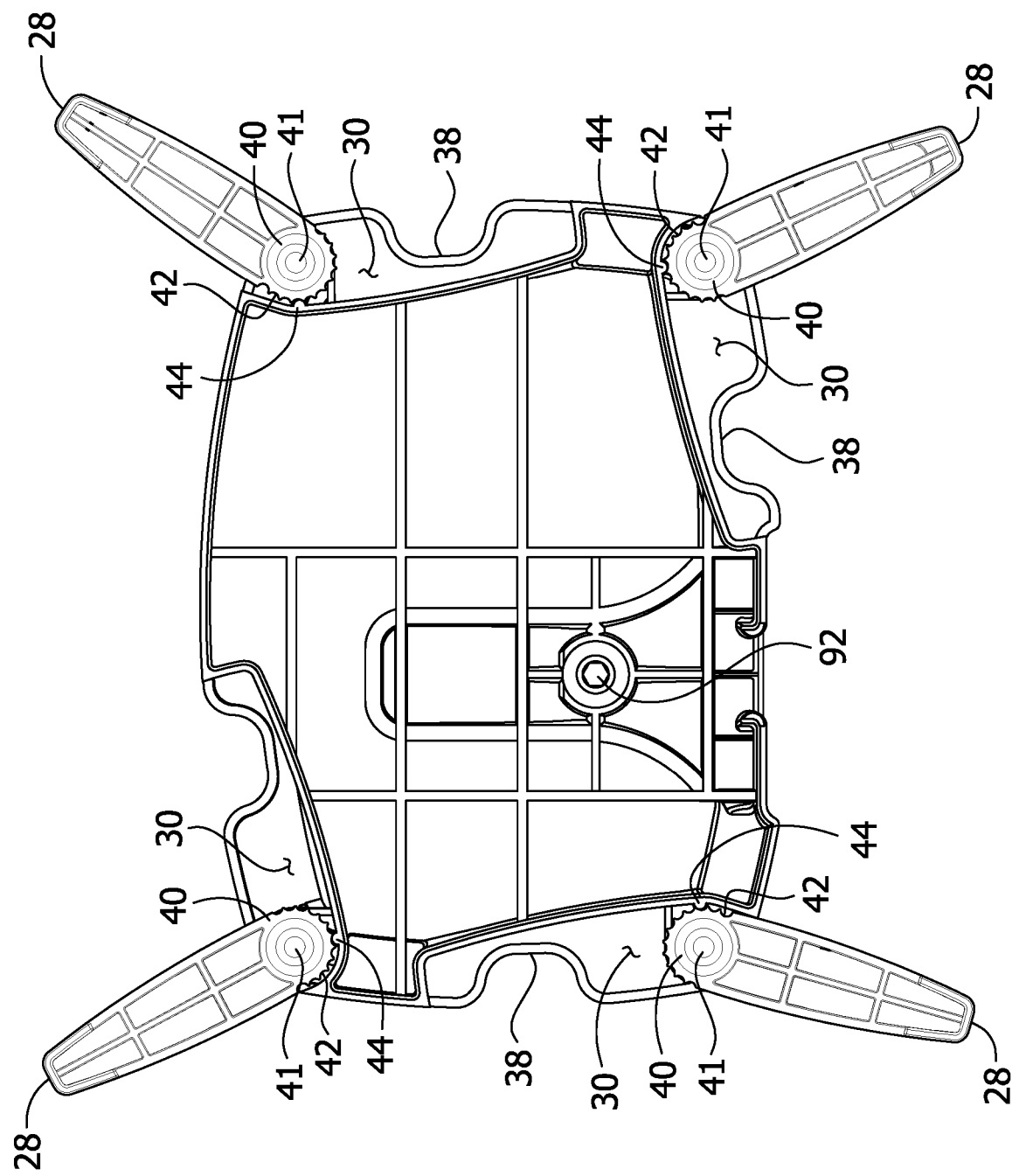
FIG. 3 is a bottom view of the support.
Figure 4:
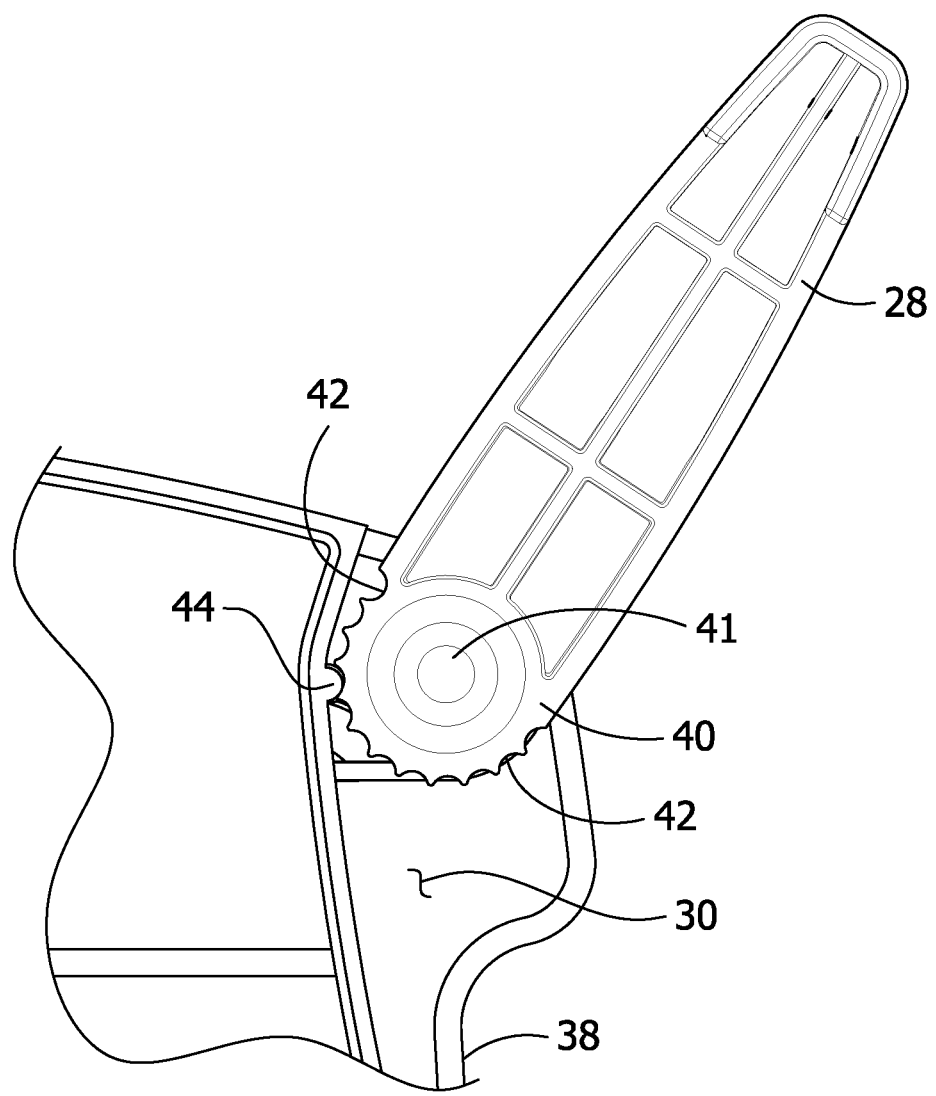
FIG. 4 is an enlarged fragmentary view of the support shown in FIG. 3.

Referring to FIGS. 3 and 4, each foot 28 may include an anchor portion 40 that is pivotably attached to the bottom of the support portion 24 by a fastener 41. The anchor portion 40 may have a plurality of indentations 42 formed around an outer surface of the anchor portion 40. A detent 44 may be formed on an inner surface of each pocket 30 and configured to be removably received in the indentations 42 to releasably hold the foot 28 in any of several positions. At least one of the anchor portion 40 and the detent 44 is resiliently deformable to permit movement of the foot from the fully stowed to the fully deployed position and back. It will be understood that the detent 44 holds the foot 28 in both the fully stowed and fully deployed positions.

Referring to FIGS. 1, 2, 10, and 11, the attachment portion 25 of the base 18 may comprise an attachment member 46 and the attachment portion may be formed integrally with the support portion 24. The attachment portion 25 may be disposed generally at the back of the support portion 24 and may extend upward from the support portion. The attachment member 46 may be fixedly attached to a remainder of the attachment portion 25. In the illustrated embodiment, the attachment member is formed as one piece with the remainder of the attachment portion 25. The attachment member 46 can be formed in other ways without departing from the scope of the disclosure.

The attachment member 46 may pivotally attach a mounting portion 50 of the medical device mounting assembly 14 to the attachment portion 25 of the base 18. The attachment member 46 may comprise a tab 52 projecting from an arcuate section 54 of the attachment portion 25. The tab 52 may include a pivot hole 56 generally at a front end of the tab and a plurality of locking holes 58 arcuately spaced from one another and extending generally along a back end of the tab adjacent the arcuate section 54 of the attachment portion 25. The locking holes 58 are arranged at an approximately constant distance from the pivot hole 56. The locking holes 58 may be arranged to provide about 45 degrees of pivot adjustment between the mounting portion 50 and the attachment member 46 about a pitch axis PI (FIG. 5) extending through the pivot hole 56. In the illustrated embodiment, the pivot hole 56 is disposed at a top of the front end of the tab 52, and a topmost locking hole 58 is disposed near a top of the back end of the tab. It is envisioned that the attachment member 46 may have other shapes and the pivot hole 56 and locking holes 58 may be disposed in other locations.

Referring to FIG. 14, the support 10 may be carried in a backpack BP within an internal compartment thereof such that a medical bag 12 is suspended by the support inside the backpack. The feet 28 of the support 10 may be moved to the stowed position (FIG. 7) to facilitate inserting the support into the backpack BP. However, the feet 28 may be moved to the deployed position (FIG. 1) and inserted into the backpack BP without departing from the scope of the disclosure. The backpack BP allows the patient the freedom to be mobile while using the support 10 and pump 16 mounted on the support. The same support 10 can be used for table top support out of the backpack BP by moving the feet 28 to the deployed position for stability.

Figure 2:
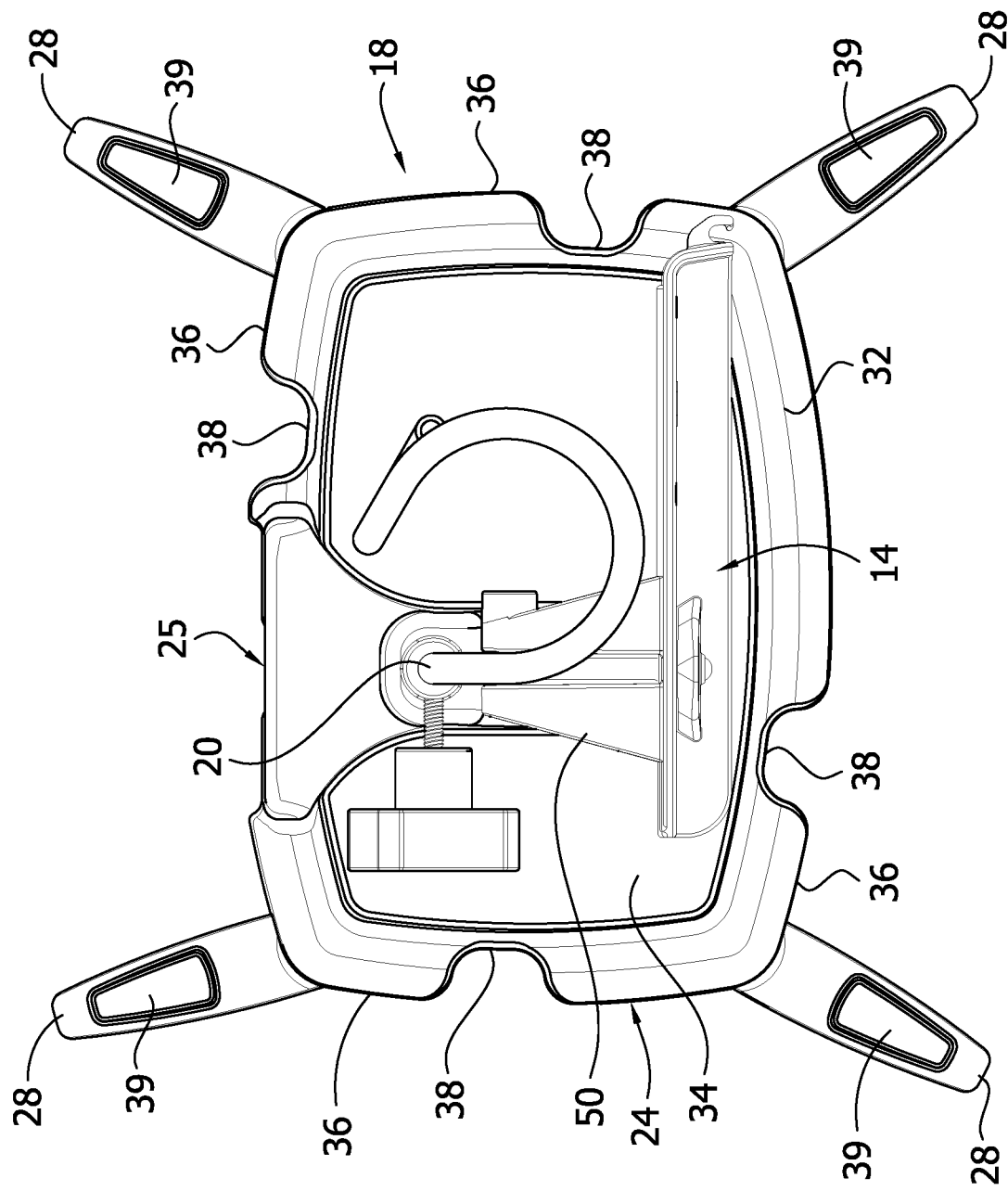
FIG. 2 is a top view of the support.
Figure 5:
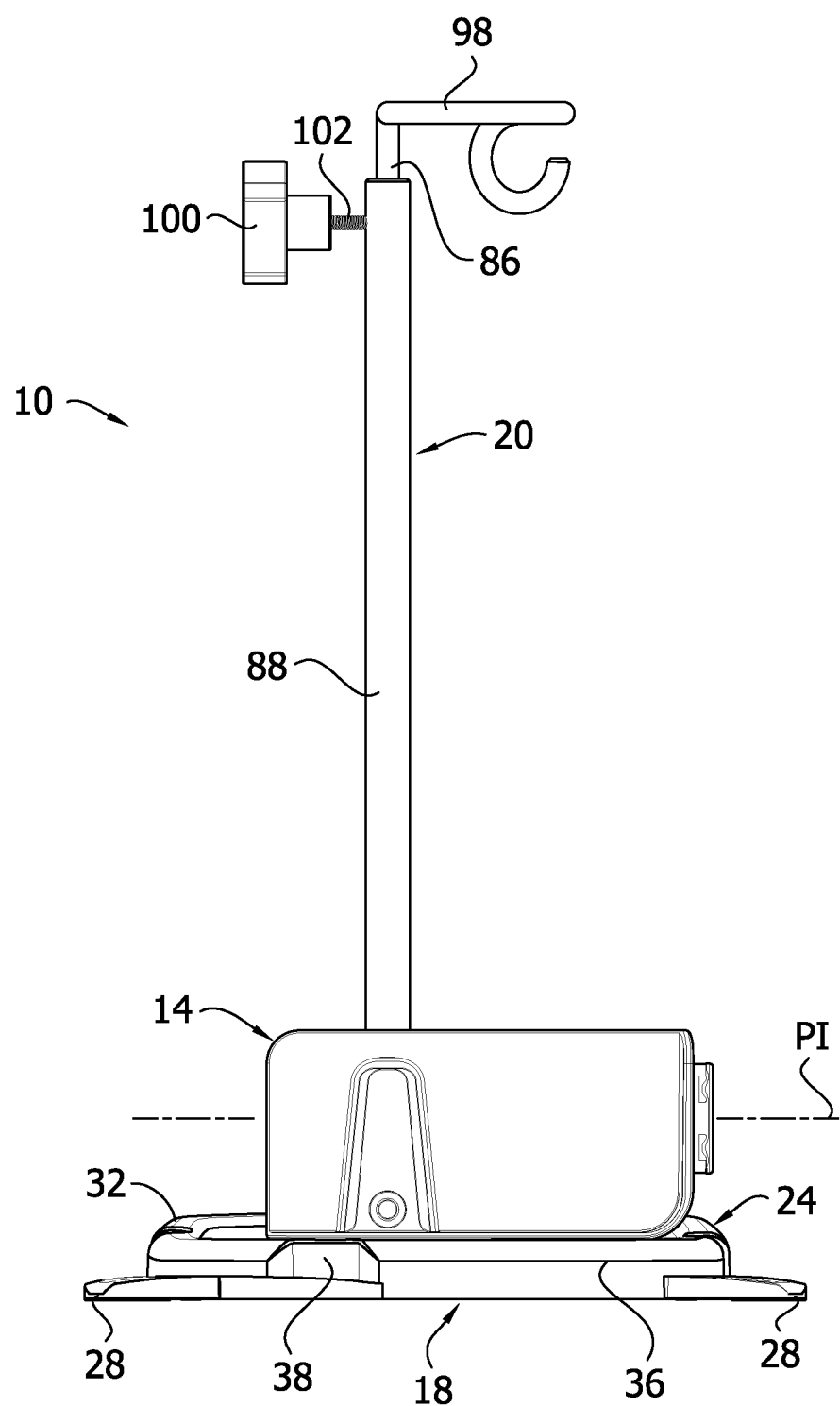
FIG. 5 is a front view of the support showing a pole assembly in a first position.
Figure 6:
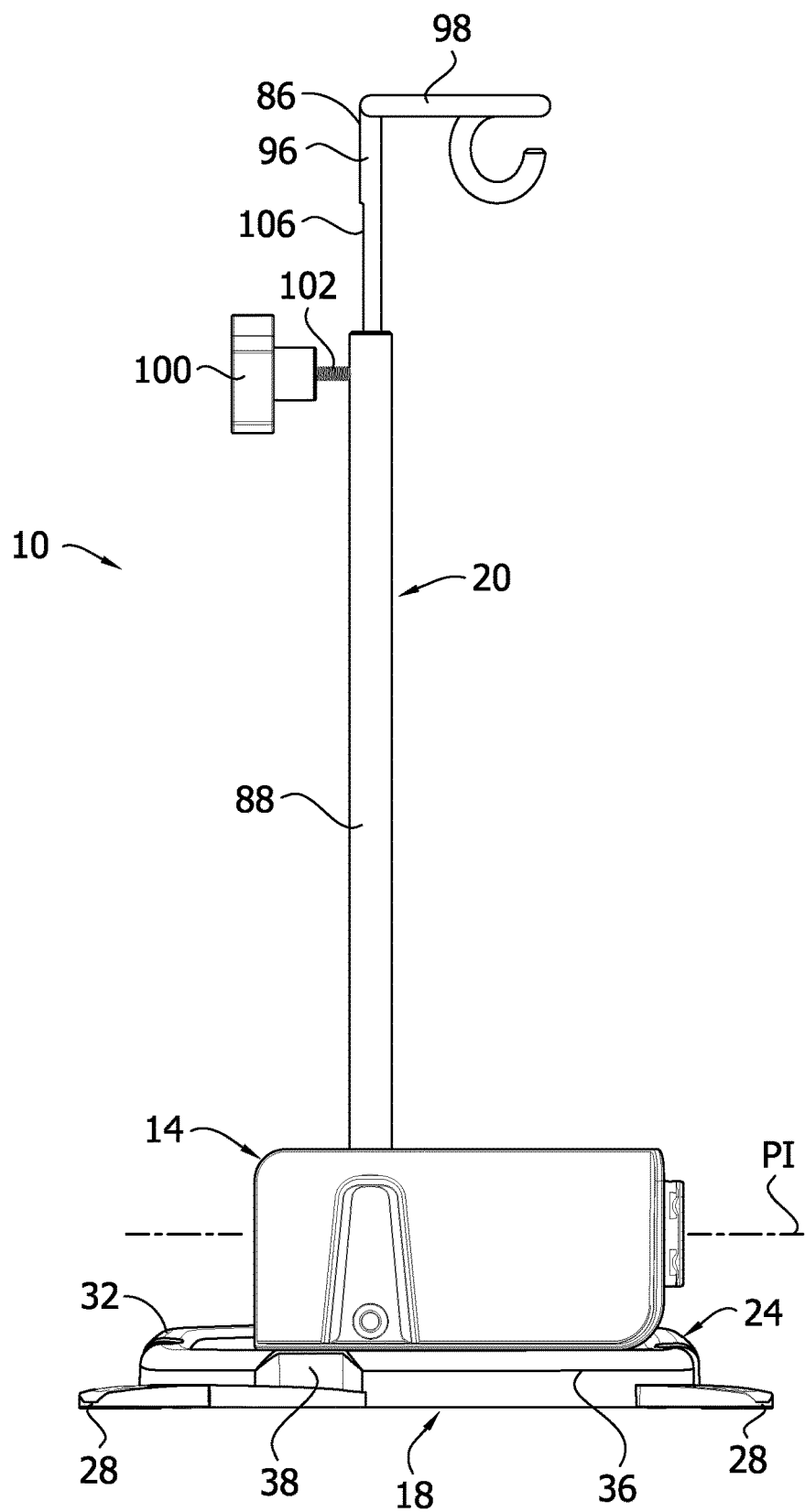
FIG. 6 is a front view of the support showing the pole assembly in a second, extended position.
Figure 12:
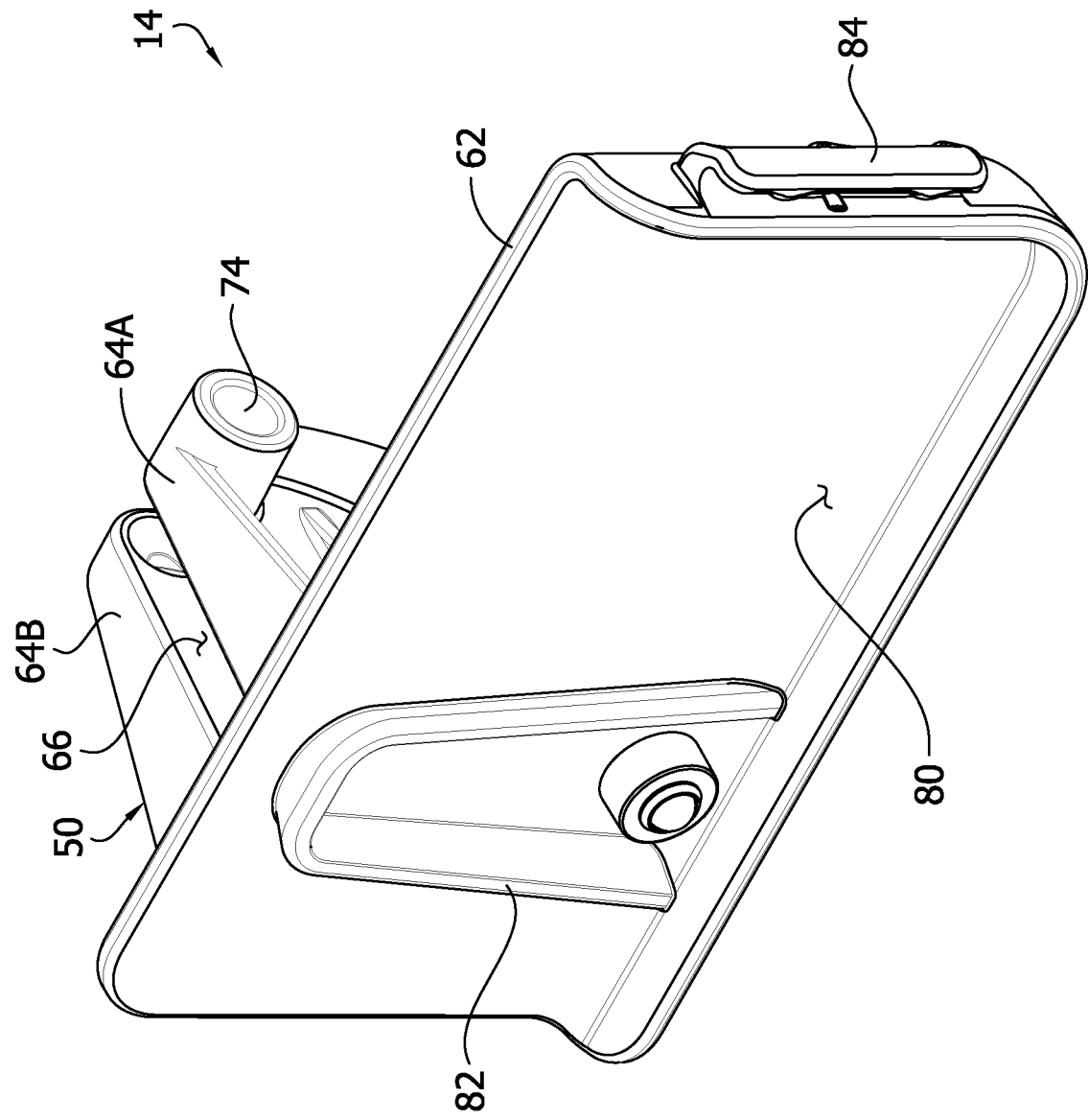
FIG. 12 is a perspective of a medical device mounting assembly of the support.
Figure 13:
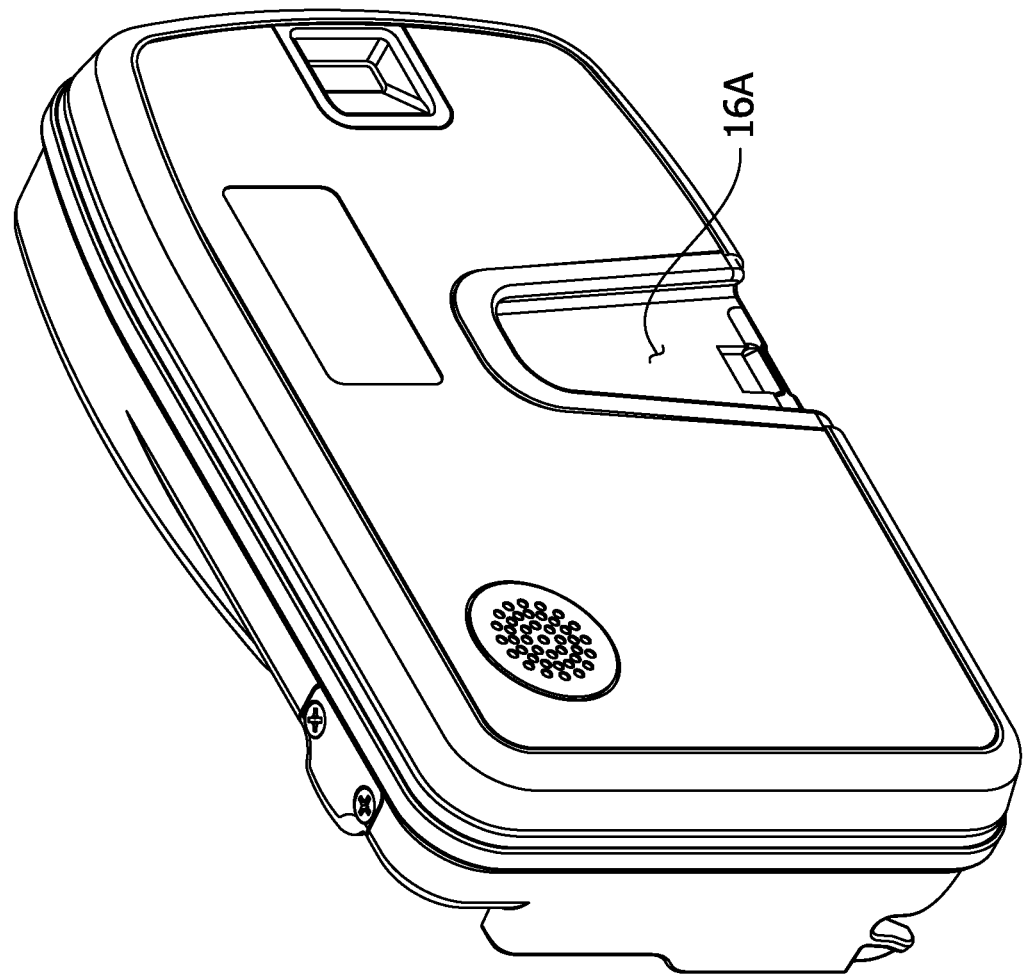
FIG. 13 is a rear perspective of an enteral feeding pump.
Figure 14:
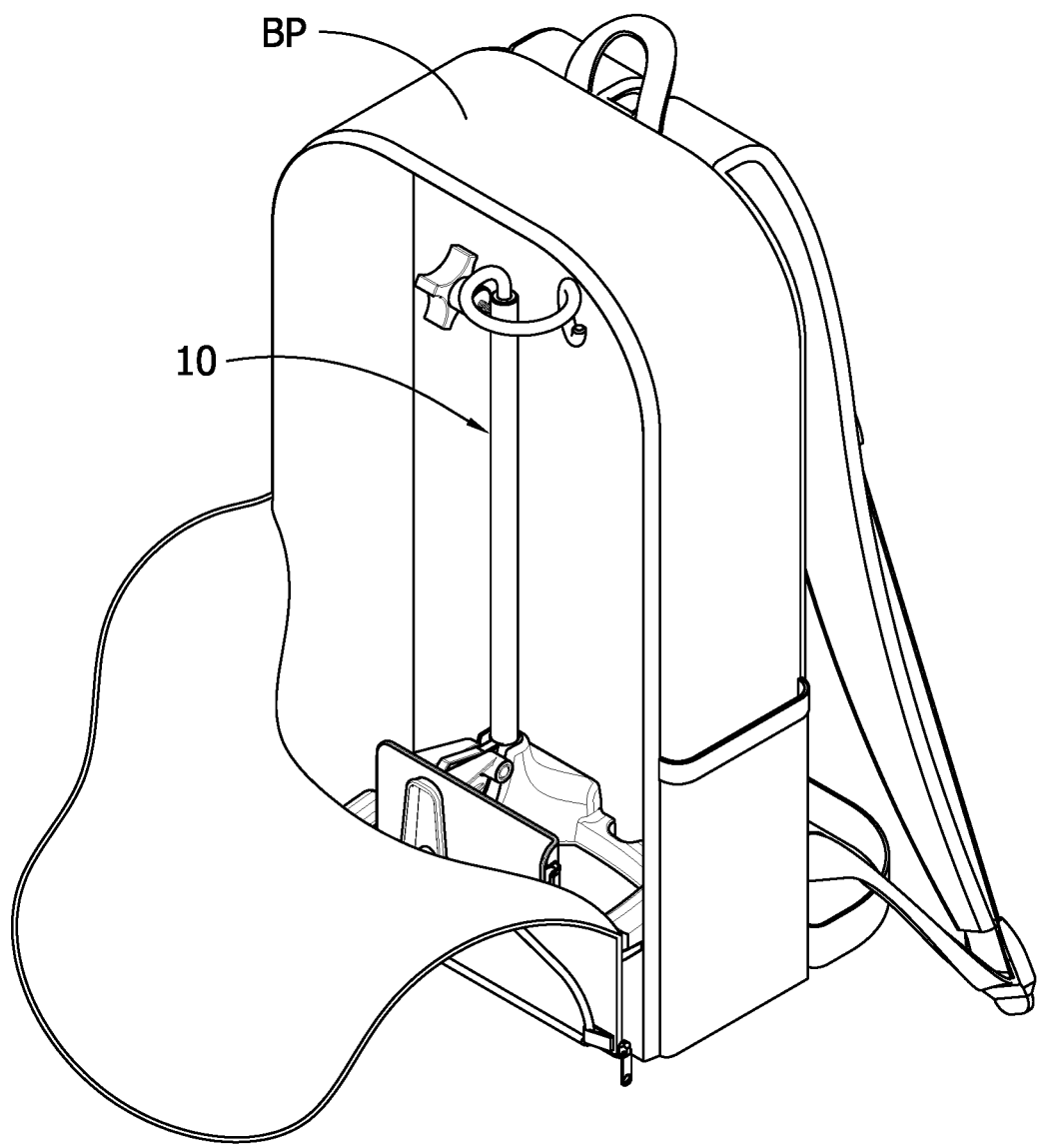
FIG. 14 is a perspective of the support of FIG. 7 shown inside a backpack.
Figure 15:
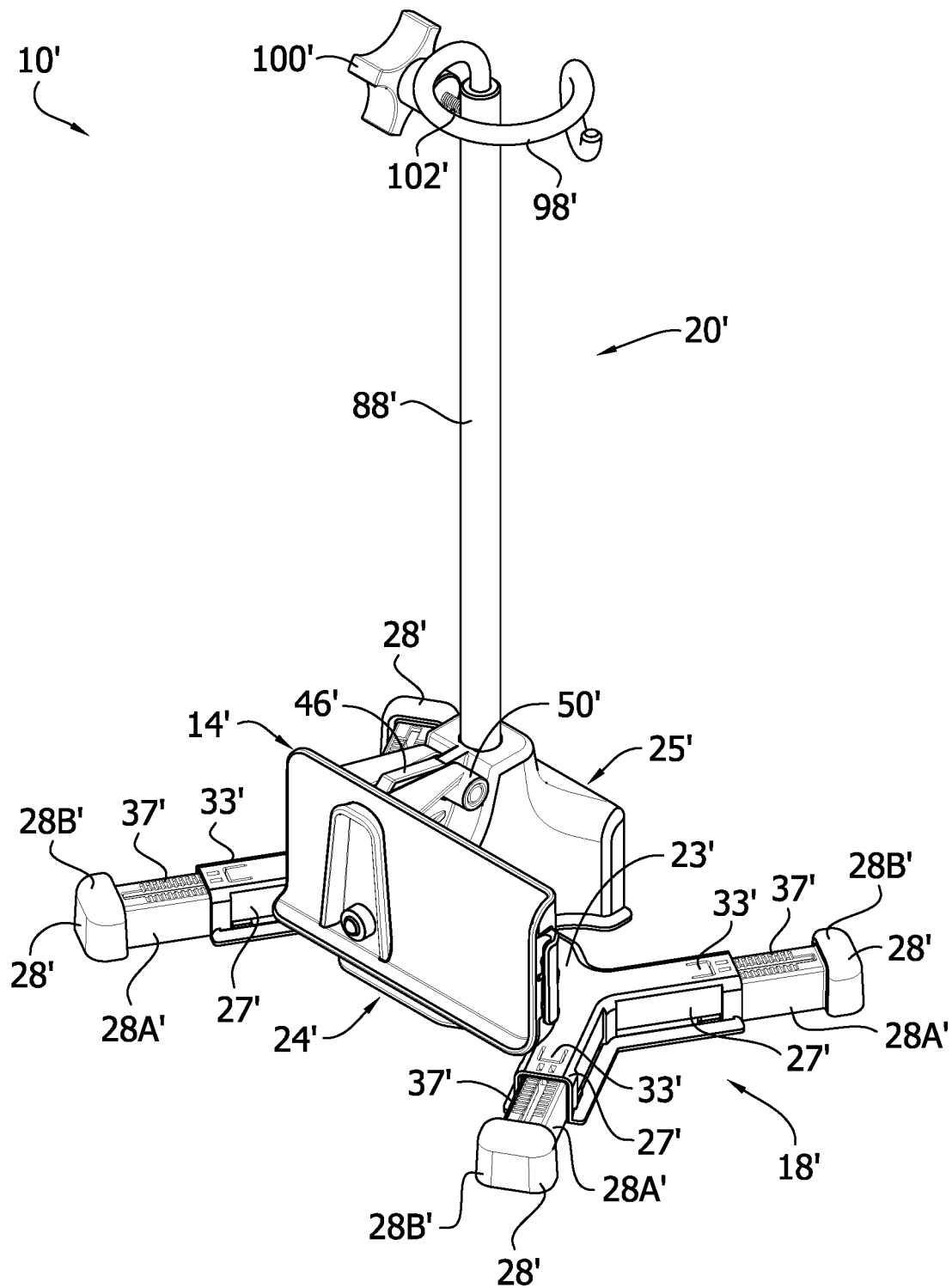
FIG. 15 is a perspective view of another embodiment of a enteral feeding bag support with feet shown in an extended position.
Figure 16:
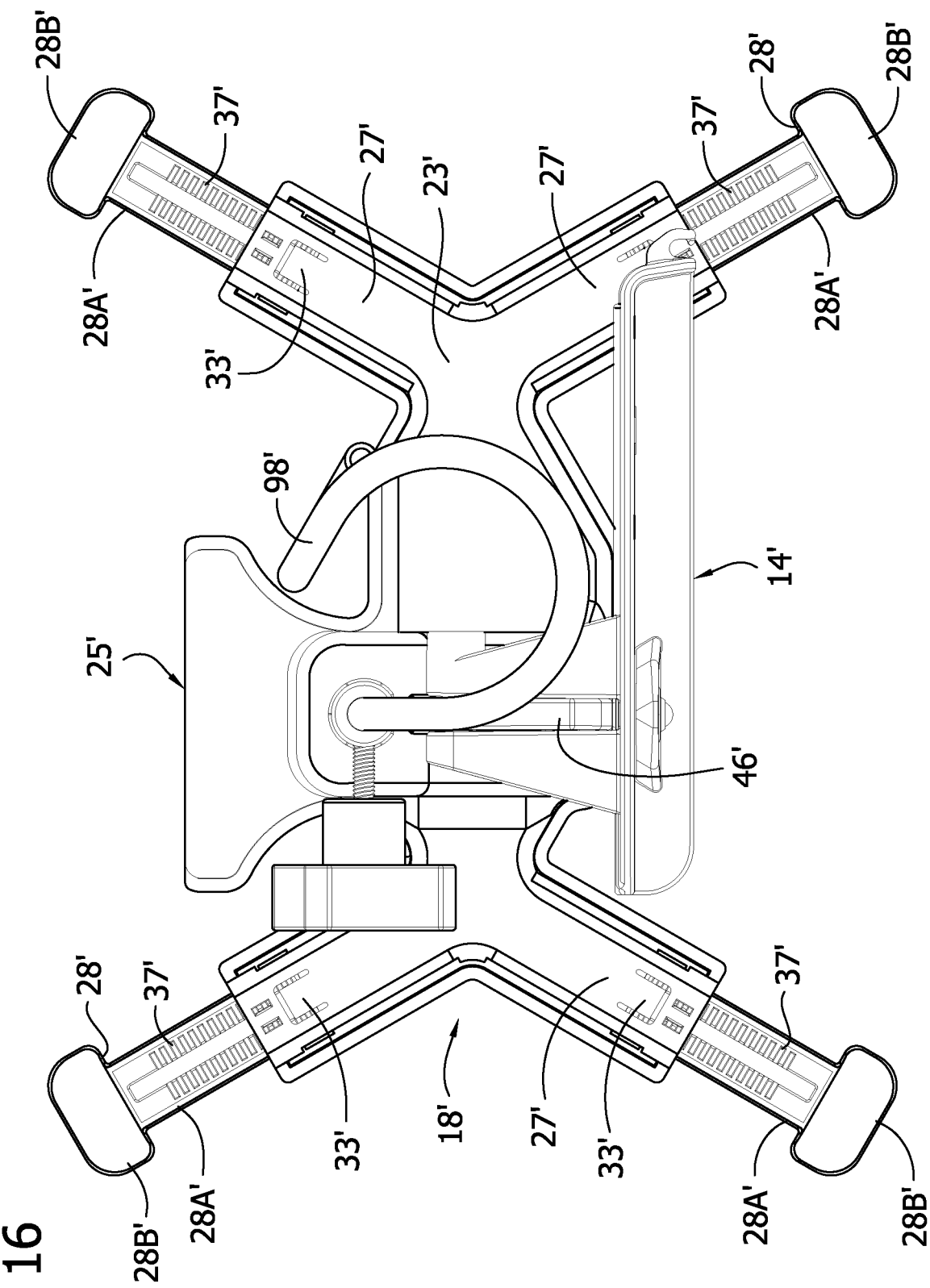
FIG. 16 is a top view of the support of FIG. 15.
Figure 17:
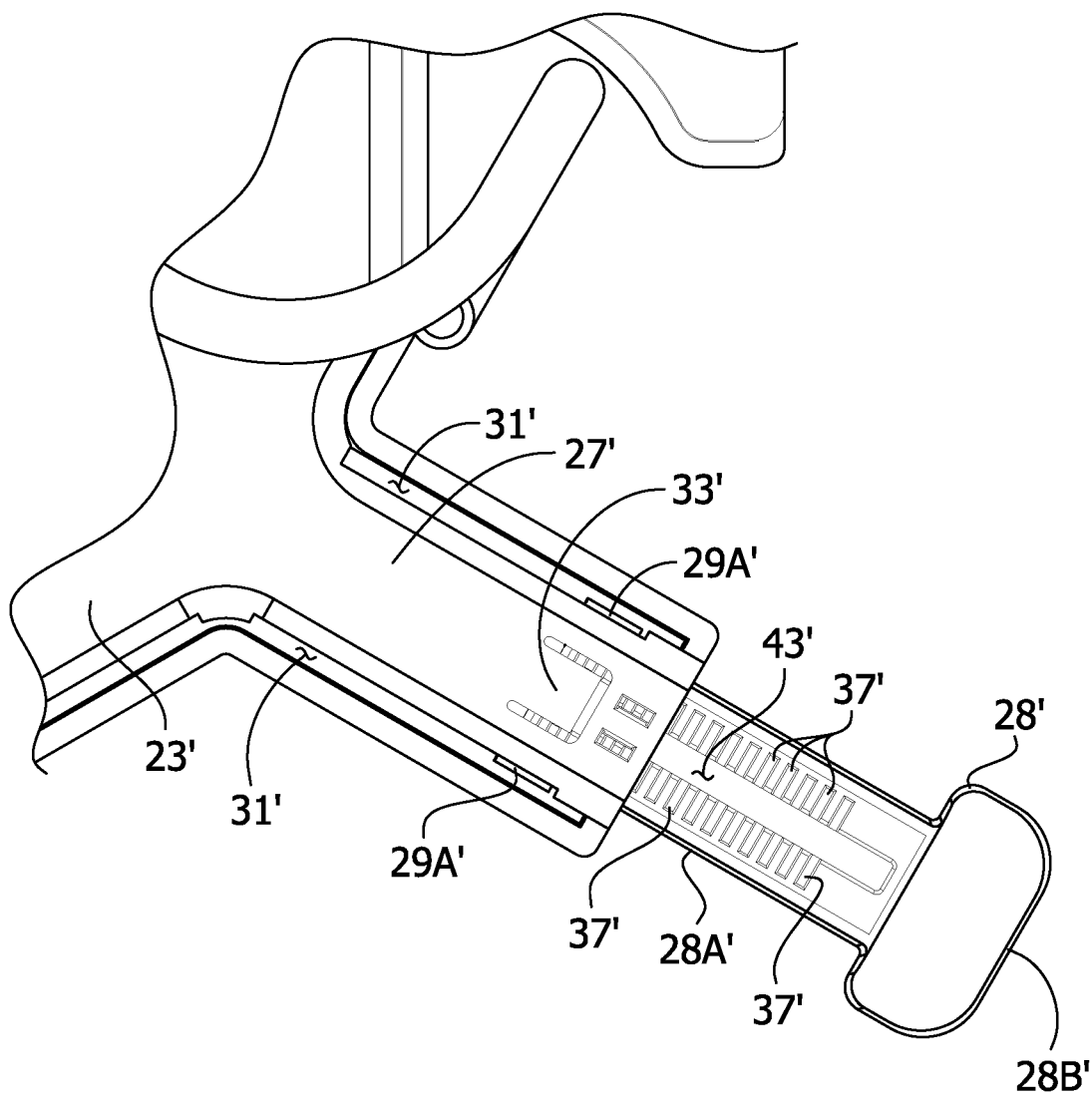
FIG. 17 is an enlarged fragmentary view of the support shown in FIG. 16.
Figure 18:
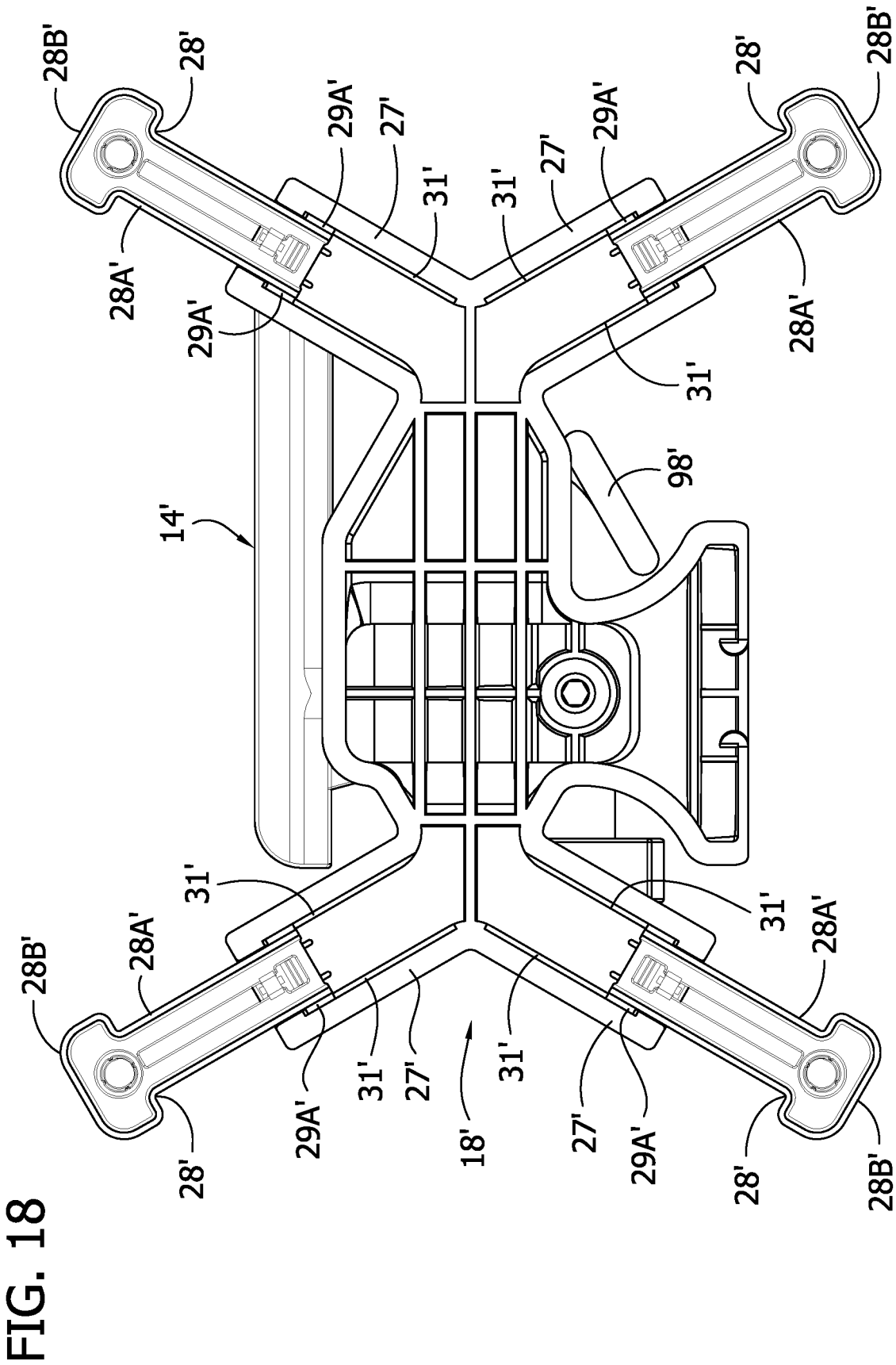
FIG. 18 is a bottom view of the support of FIG. 15.
Figure 19:
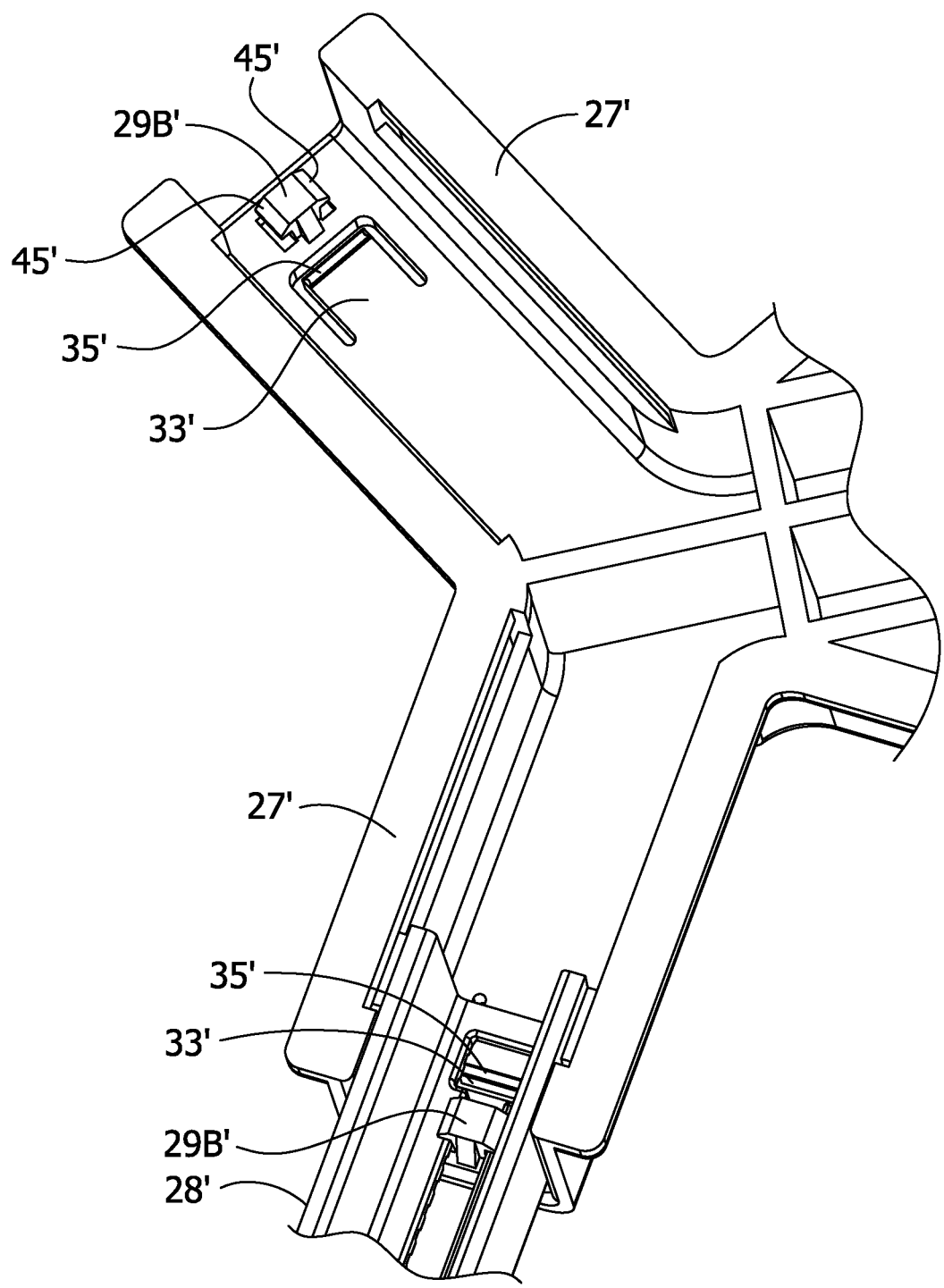
FIG. 19 is an enlarged fragmentary bottom perspective view of the support shown in FIG. 17 with a foot of the support removed to show underlying detail.
Figure 20:
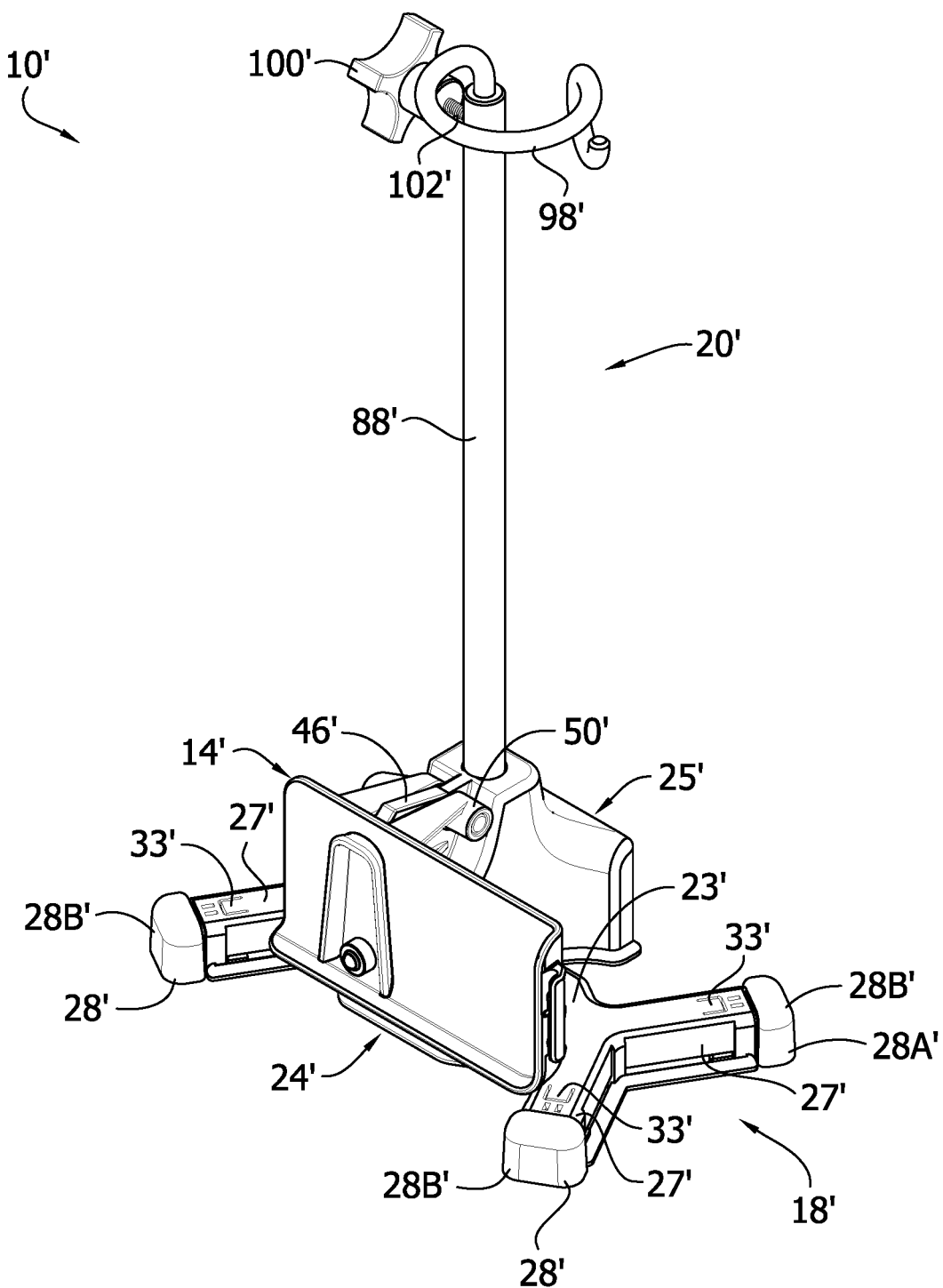
FIG. 20 is a perspective view of the enteral feeding bag support of FIG. 15 with the feet shown in a retracted position.
Figure 21:
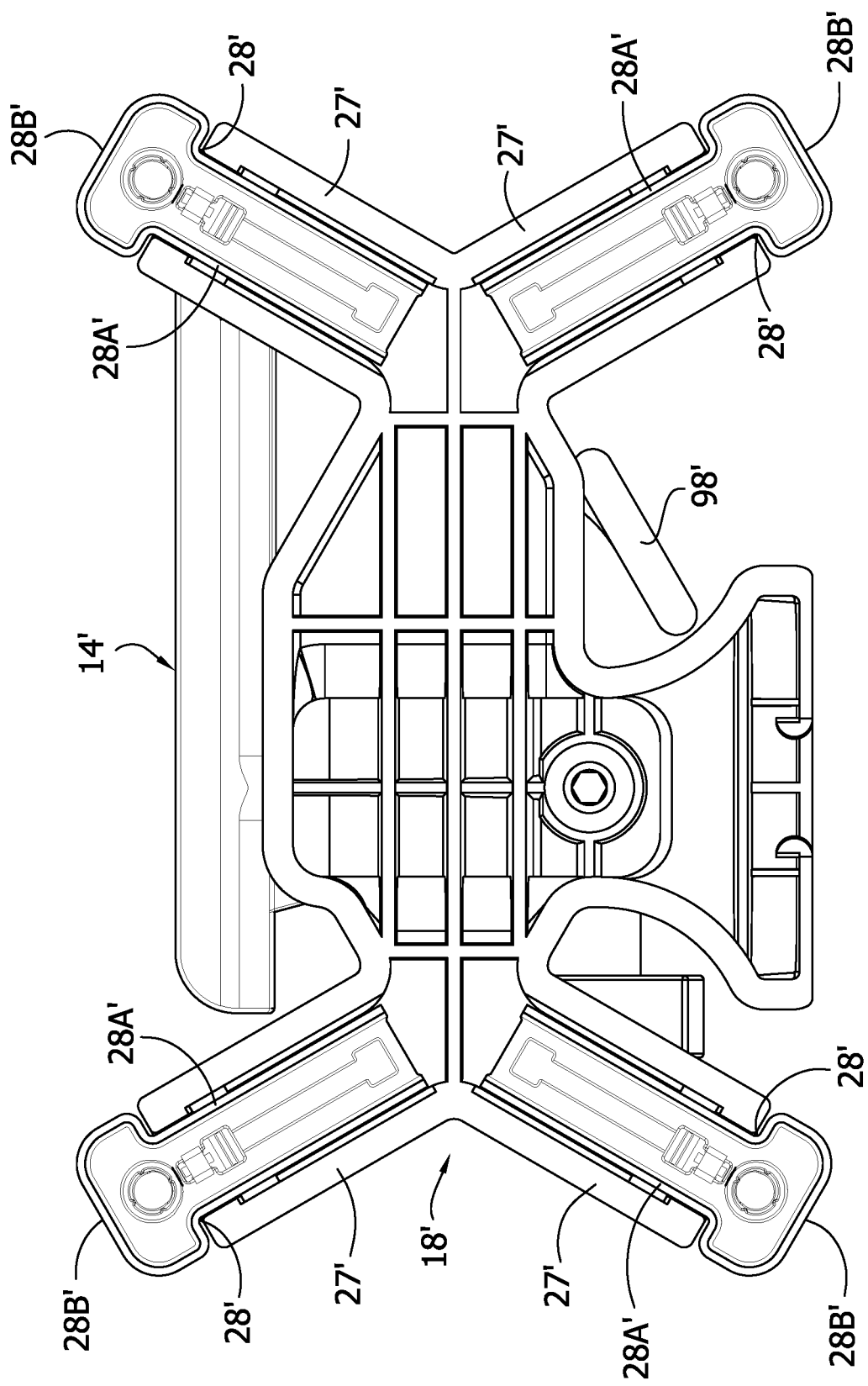
FIG. 21 is a bottom view of the support of FIG. 20.
Figure 22:
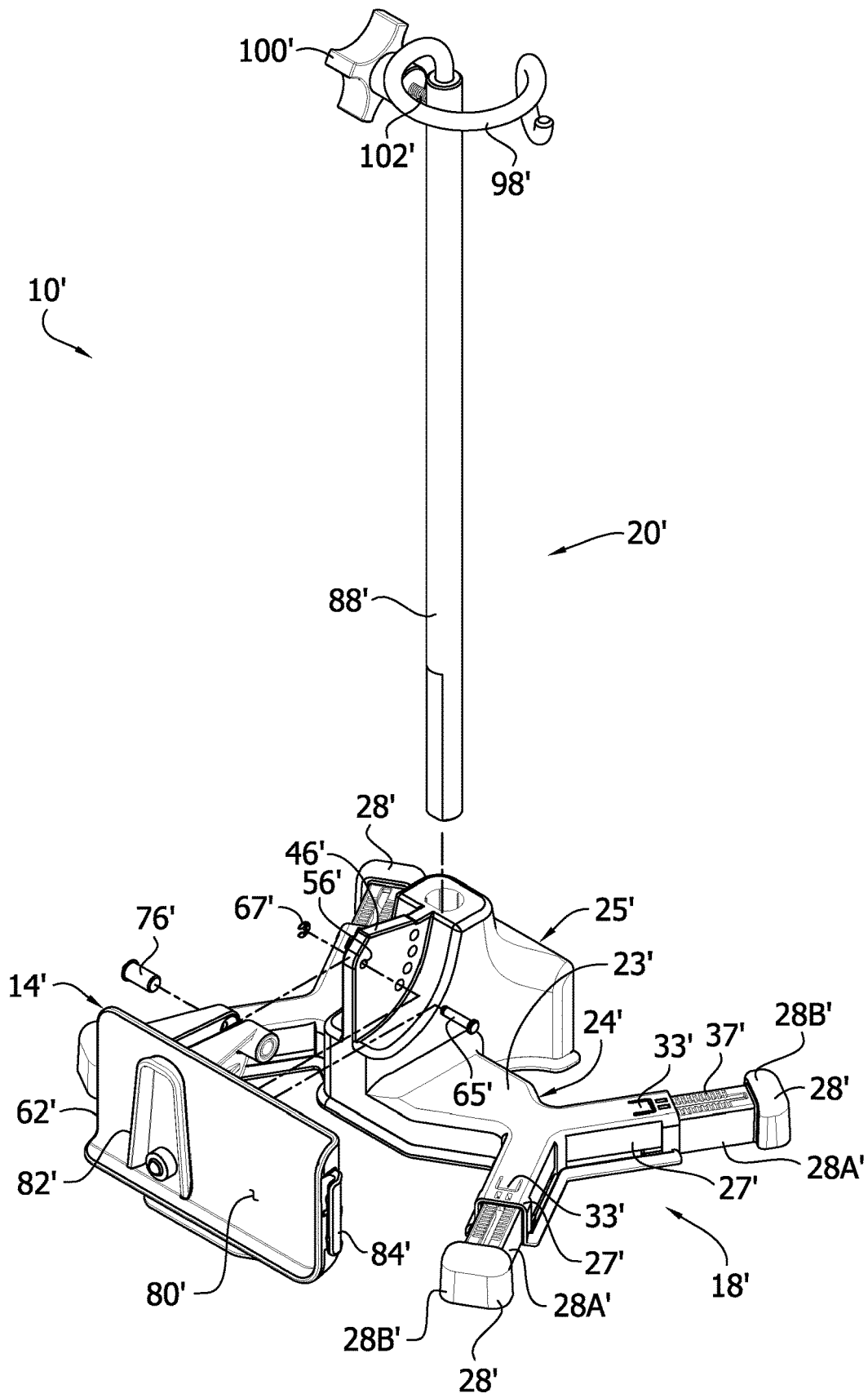
FIG. 22 is an exploded view of the support of FIG. 15.
Figure 23:
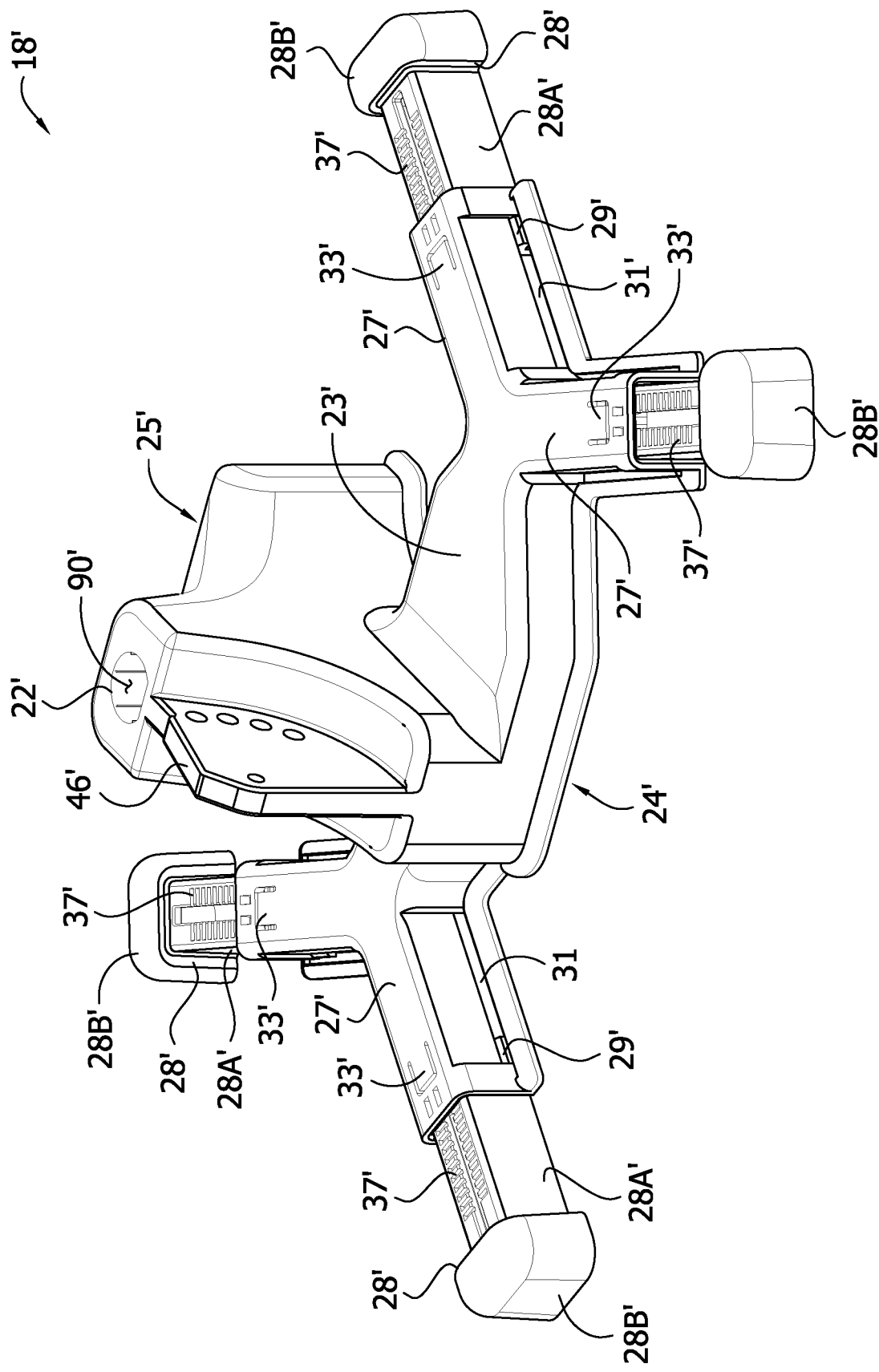
FIG. 23 is a perspective of a base of the support of FIG. 22.

Referring to FIGS. 1, 2, 9, and 12, the medical device mounting assembly 14 may comprise the mounting portion 50 for attaching to the attachment member 46 of the attachment portion 25, and a device receiving platform 62 for releasably attaching a medical device, such as the enteral feeding pump 16 shown in FIG. 13. The pump 16 can be mounted so that it can be tilted up or down as is convenient for viewing and/or manipulation. The mounting portion 50 may comprise a pair of spaced apart arms 64A, 64B defining a channel 66 sized to receive at least a portion of the tab 52 of the attachment member 46. The arms 64A, 64B may have aligned holes (not shown) near respective bases of the arms for receiving a pivot pin 65 to mechanically link the mounting portion 50 to the attachment member 46 for rotation about the pitch axis PI. The pivot pin 65 may be secured in the pivot hole 56 and aligned holes by a C-clip 67. In particular, the pivot pin 65 may extend through the pivot hole 56 in the attachment member 46 and the aligned holes in the mounting portion 50 to pivotally link the medical device mounting assembly 14 to the attachment member. This connection allows the mounting assembly 14 to pivot relative to the attachment member 46 about the pitch axis PI. The channel 66 may have a width only slightly larger than a thickness of the tab 52 to substantially inhibit movement of the mounting portion 50 relative to the tab along a single pivot axis P1 (FIGS. 2 and 5).

A detent hole 74 may be disposed near the top of arm 64A for receiving a locking detent 76 (FIG. 9). The locking detent may be adapted for selective engagement with the locking holes 58 in the attachment member 46. The detent 76 may also be spring loaded such that a tip of the detent is movable relative to a base of the detent. When the detent 76 is received in one of the locking holes 58 and a torque of magnitude more than a threshold above the torque applied by the weight of the medical device mounting assembly 14 plus the weight of the enteral feeding pump 16 (when attached thereto) is applied to the mounting portion, a lip of the locking hole 58 may engage the tip of the detent 76 and move the tip of the detent into the base providing a clearance for the device attachment portion to pivot relative to the attachment member 46. Upon coming into registration with an adjacent locking hole 58, the spring loaded detent 76 may urge the tip into the hole to again releasably lock the mounting portion 50 in place on the attachment member 46. The locking detent 76 may have other configurations allowing the detent to releasably engage the locking holes 58 in the attachment member 46.

The device receiving platform 62 of the medical device mounting assembly 14 may form a pocket 80 (FIG. 12). A device mount 82 may be disposed on a rear wall of pocket 80 releasably attaching the enteral feeding pump 16 to the support 10 by being removably received in a recess 16A on the back of the pump. A tube holder 84 may be disposed on a side wall of the pocket 80 to retain medical tubing extending to or from the pump 16.

In the illustrated embodiments, the pole assembly 20 has a selectively adjustable height. Referring to FIGS. 1-3 and 5-8, the pole assembly 20 may be inserted into the opening 22 in the attachment portion 25 of the base 18. The pole assembly 20 may comprise an inner tube member 86 and an outer tube member 88 surrounding at least a portion of the inner tube member. At least the outer tube member 88 extends into the opening 22 in the base 18. However, in at least one configuration both the outer tube member 88 and the inner tube member 86 extend into the opening 22. In the illustrated embodiment, the outer tube member 88 extends through the opening 22 and into a passage 90 in the base 18. The passage 90 extends from the opening 22 in the top of the attachment portion 18 to the bottom of the support portion 24. The outer tube member 88 may be secured in the passage 90 with a screw 92 (FIGS. 3 and 8) inserted through the base 18 into the passage 90 at the bottom of the support portion 24. The screw 92 may engage a threaded bottom portion (not shown) of the outer tube member 88 to secure the outer tube member in the passage 90.

The inner tube member 86 may include a first straight section 96 (FIG. 6) received in the outer tube member 88 and a second curved section 98 extending from the first straight section for attaching the medical bag 12 to the pole assembly 20. When the medical bag 12 is attached to the second curved section 98 and the base 18 is supported on a support surface, the medical bag is suspended above the support surface by the pole assembly 20. The inner tube member 86 is slidably received in the outer tube member 88 for adjusting a height and position of the second curved section 98 relative to the support surface. A knob 100 and screw 102 can lock the inner tube member 86 at a selected height and position relative to the support surface. Locking the inner tube member 86 in place can be achieved by rotating the knob 100 in a locking direction to advance the screw 102 in a threaded hole in the outer tube member 88 to engage the screw with a flat surface 106 (FIG. 6) of the inner tube member to secure the inner tube member at a selected height and position. To unlock the inner tube member 86 to adjust its relative height and position, the knob 100 is rotated in an unlocking direction to disengage the screw 102 with the inner tube member to allow the inner tube member to freely slide relative to the outer tube member 88. The relative height and position of the inner tube member 86 can be adjusted and locked in other ways without departing from the scope of the disclosure.

Referring to FIGS. 15-24, an enteral feeding bag support of a second embodiment is indicated generally at 10'. The support 10' of the second embodiment is similar to the support 10 of the first embodiment except as described hereinafter. Accordingly, like components are indicated by corresponding reference numerals followed by a prime. The support 10' may comprise a base 18' for resting on a surface (not shown), and a pole assembly 20' configured for attachment to the base to suspend a medical bag (not shown) above the support surface. The base 18' may comprise a support portion 24' for supporting the support 10' on the support surface and an attachment portion 25' for attaching the pole assembly 20' to the base and movably attaching a medical device mounting assembly 14' to the base. The support portion 24' may be configured to engage the support surface. The support portion 24' may include a body 23' and legs 27' extending from the body. Feet 28' may be attached to the legs 27' for engaging the support surface to stabilize the support 10' on the support surface. The feet 28' may each include a first portion 28A', a least a portion of which is received in a respective leg 27' in telescoping fashion. A second portion 28B' of the foot 28' is wider than the first portion 28A' and disposed on an end of the first portion. The wider second portion 28B' can provide added stability to the support 10'.

Referring to FIGS. 15-20, each foot 28' is slidably attached to a respective leg 27' of the support portion 24' and movable along a longitudinal axis of the leg between retracted and extended positions. The sliding movement of each foot 28' may be guided through the engagement of first slide members 29A' disposed on the first portion 28A' of the foot 28' and channels 31' formed in the legs 27'. As the feet 28' are moved relative to the legs 27', the first slide members 29A' slide along the channels 31' guiding the movement of the feet. A second slide member 29B' on the legs 27' slides along a channel 43' in the first portion 28A' of the feet 28'. The second slide member 29B' is retained in the channel 43' by hooks 45' on the second slide member. The engagement between the second slide members 29B' and the channels 43' also guides the sliding movement of the feet 28' relative to the legs 27'. In the illustrated embodiment, the hooks 45' are formed integrally with a remainder of the second slide member 29B'. The hooks 45' could be formed separately from the second slide member 29B' and attached to the second slide member by suitable means.

Each foot 28' can be selectively and releasably locked in incremental positions along the longitudinal axes of the legs 27'. In the illustrated embodiment, the legs 27' each have tabs 33' including a rounded projection 35' configured to releasably engage in any one of slots 37' in the feet 28'. A pulling or pushing force of a sufficient amount on one of the feet 28' along the longitudinal axis of the respective leg 27' can cause the tab 33' on the leg to resiliently flex as the projection 35' engages an edge of a slot 37' in the foot moving the projection out of the slot and into an adjacent slot 37'. Each foot 28' can be individually pushed or pulled to place the foot in a selected position. The feet 28' could be fixedly attached to the support portion 24' without departing from the scope of the disclosure. In the illustrated embodiment, there are four feet 28' attached to the support portion 24'. However, any number of feet is envisioned.

Figure 24:
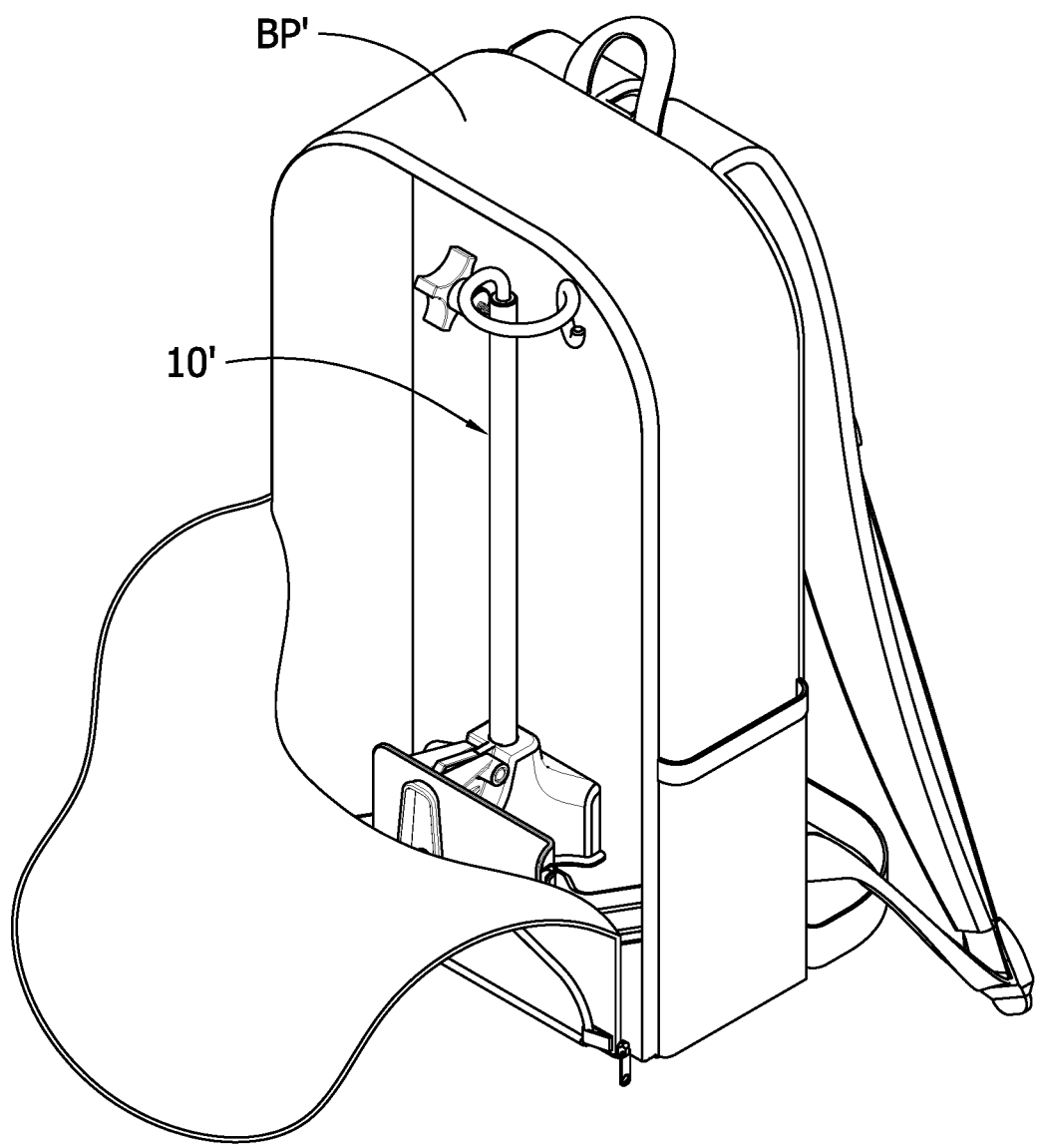
FIG. 24 is a perspective of the support of FIG. 20 shown inside a backpack.

Referring to FIG. 24, the support 10' may be carried in a backpack BP such that a medical bag (not shown) is suspended by the support inside the backpack. The feet 28' of the support 10' may be moved to the retracted position (FIG. 20) to facilitate inserting the support into the backpack BP. However, the feet 28' may be moved to the deployed position (FIG. 15) and inserted into the backpack BP without departing from the scope of the disclosure. The backpack BP allows the patient the freedom to be mobile while using the support 10' and a pump mounted on the support.

Figure 25:
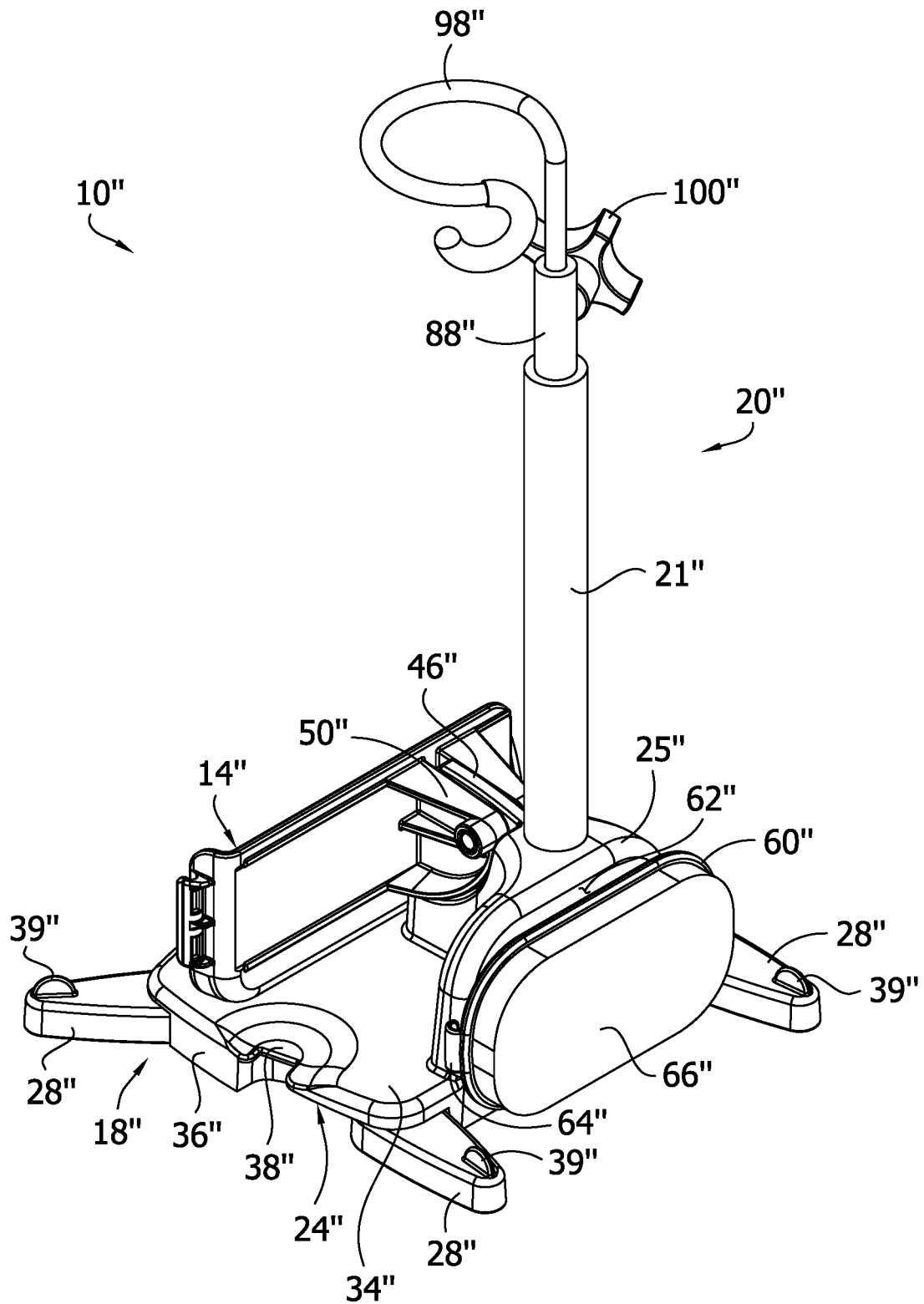
FIG. 25 is a perspective view of another embodiment of an enteral feeding bag support with feet shown in a deployed position.
Figure 32:
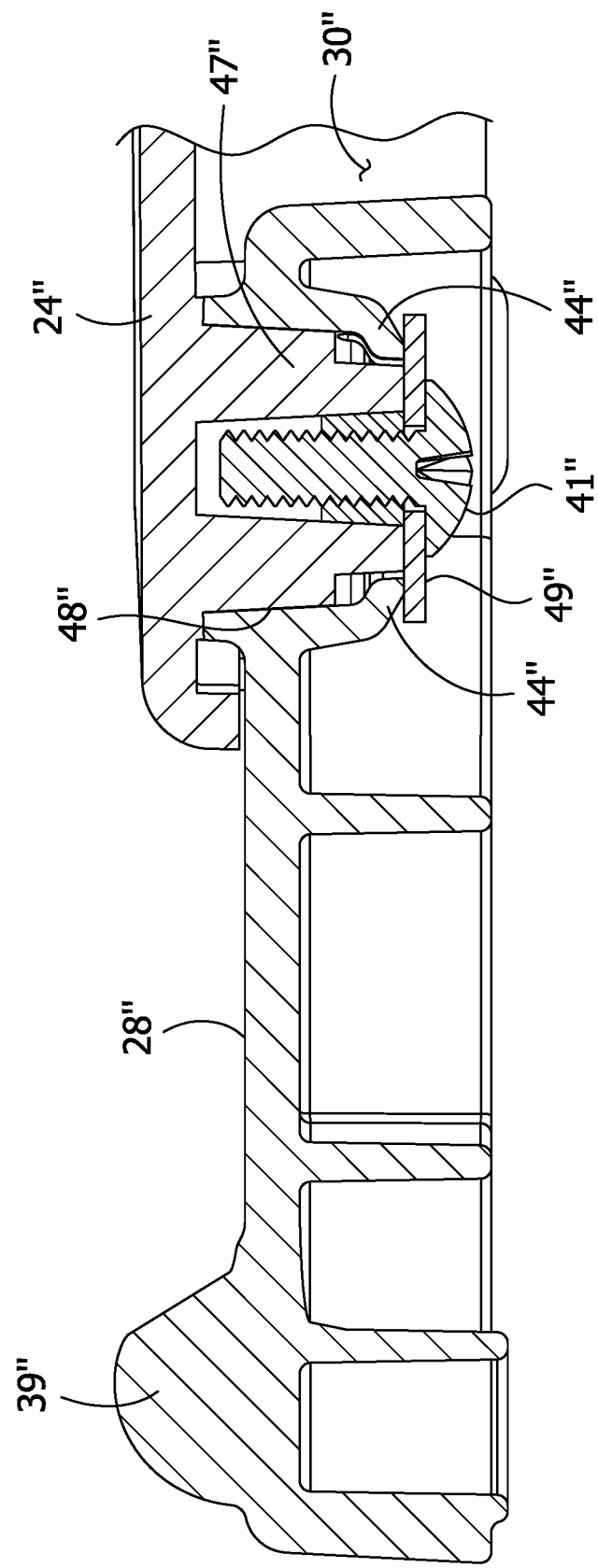
FIG. 32 is an enlarged fragmentary section of the support.
Figure 33:
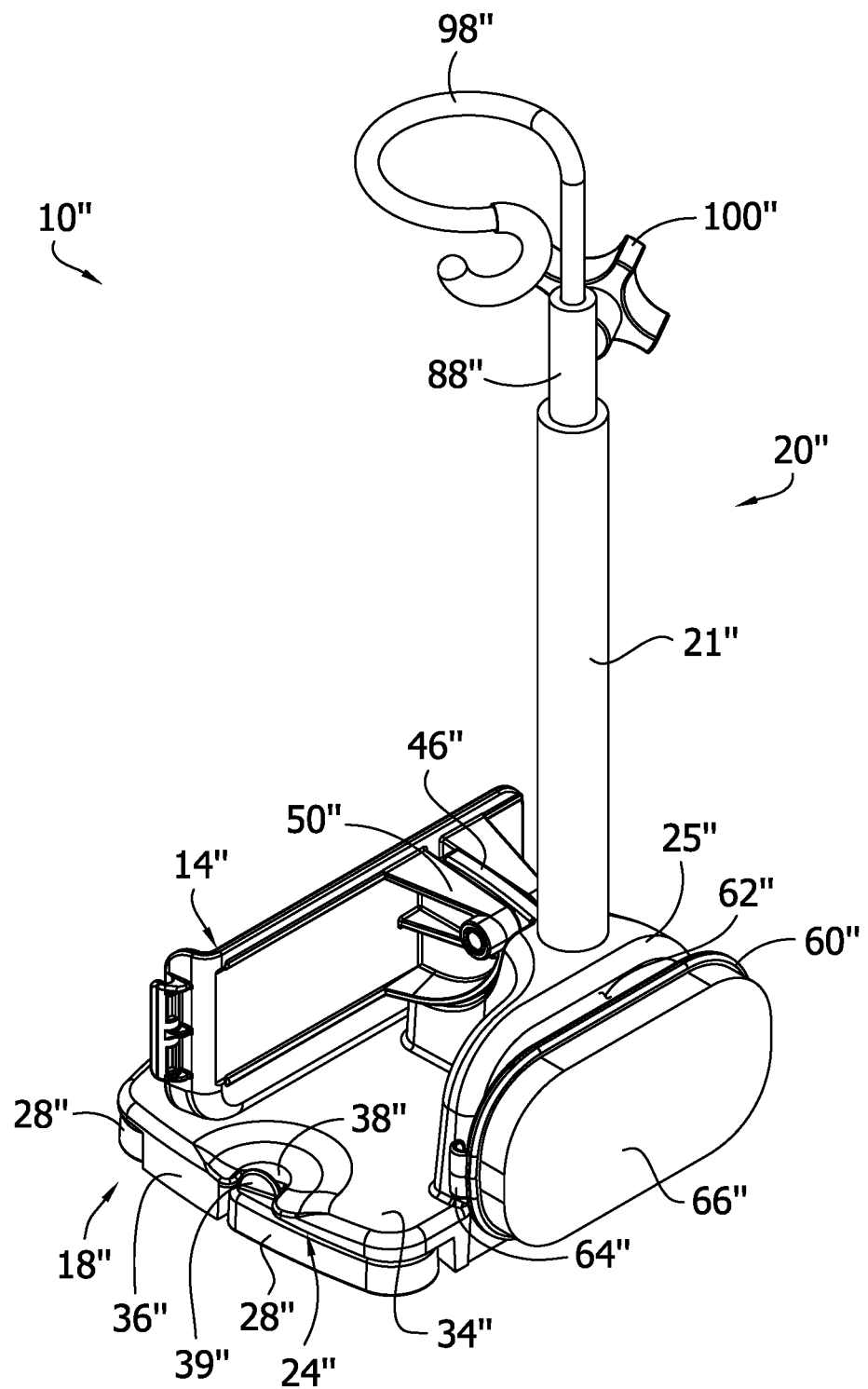
FIG. 33 is a perspective of the support of FIG. 25 with feet shown in a stowed position.
Figure 34:
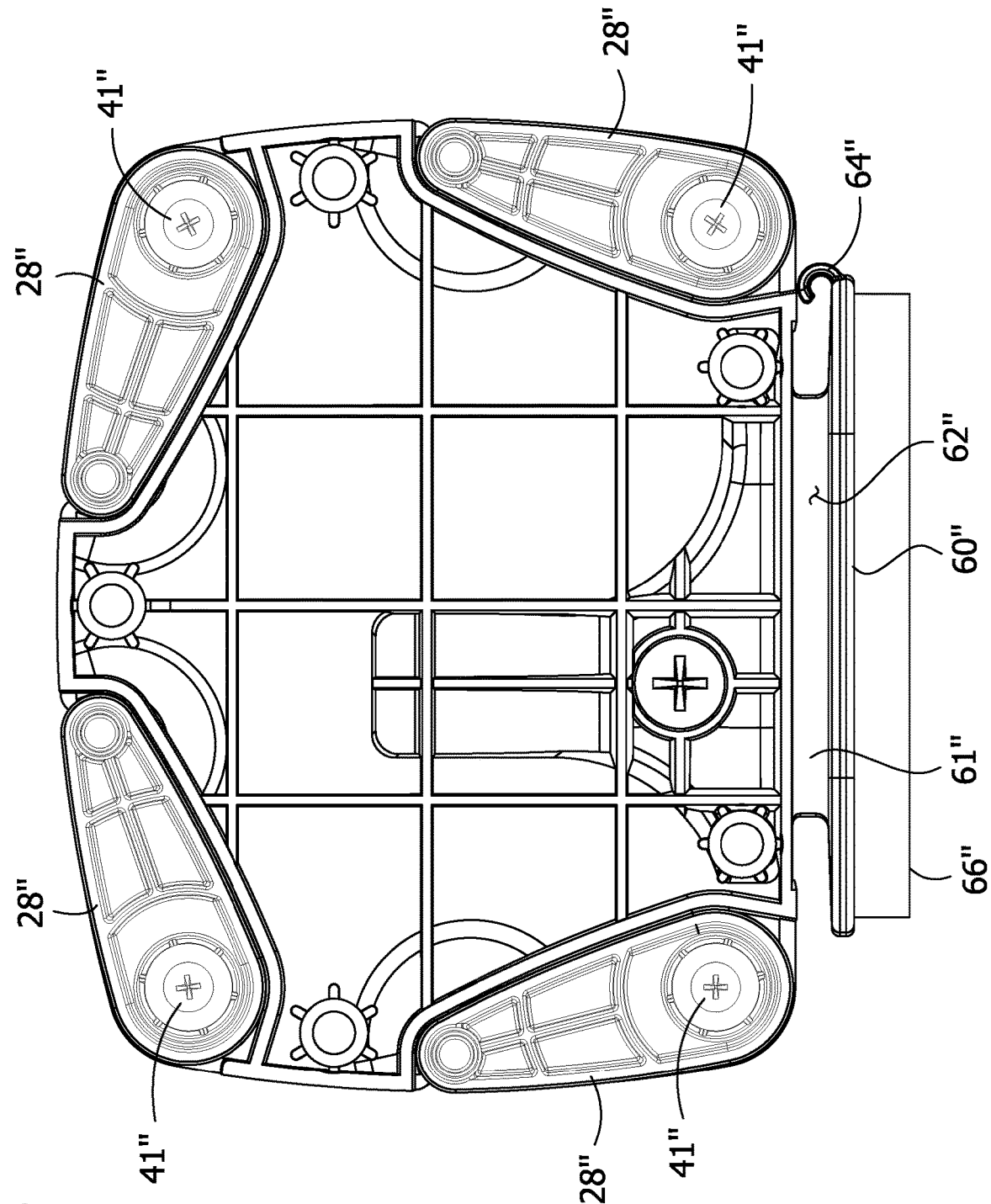
FIG. 34 is a bottom view of the support of FIG. 33.
Figure 35:
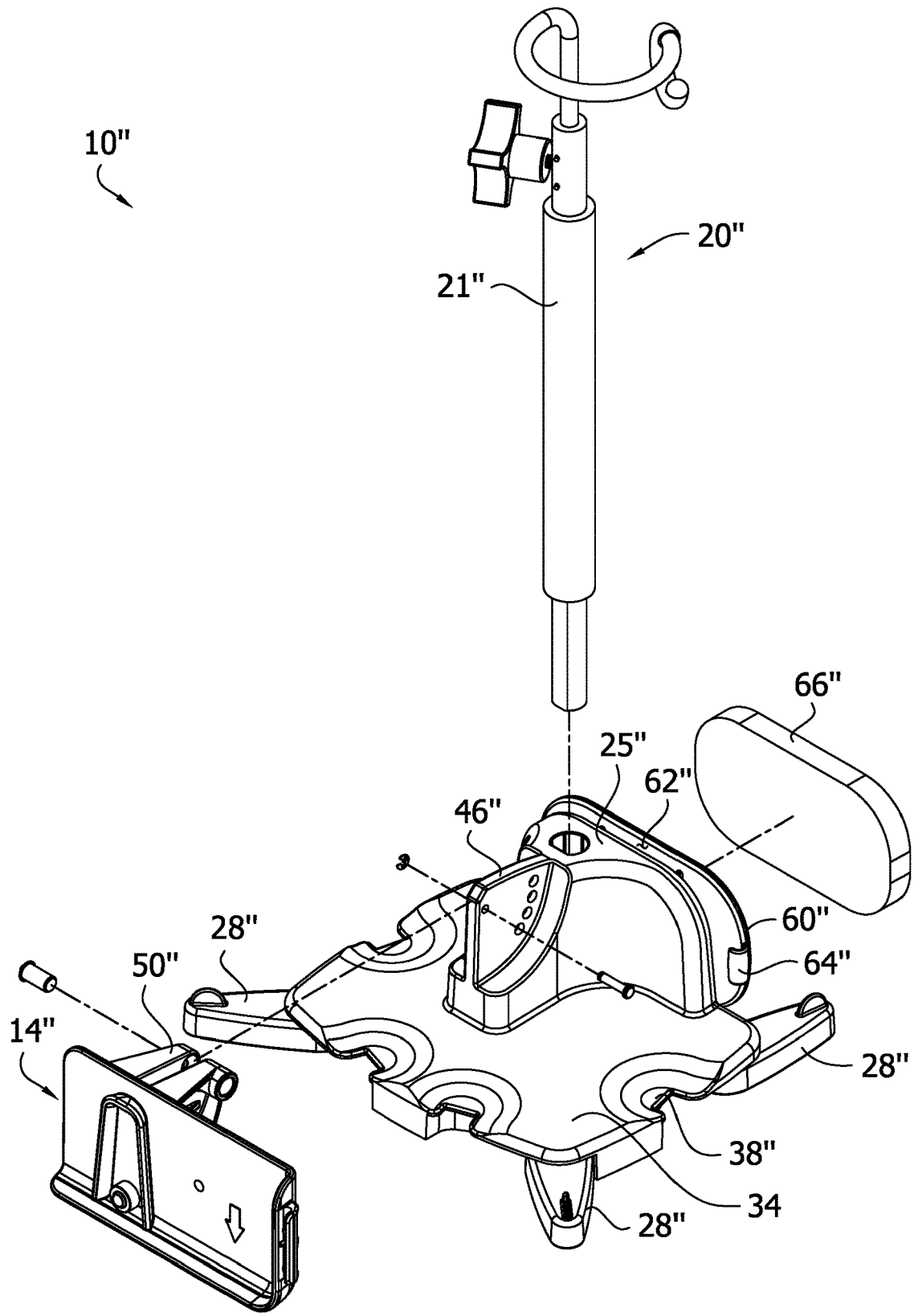
FIG. 35 is an exploded view of the support of FIG. 25.

Referring to FIGS. 25-38, an enteral feeding bag support of a third embodiment is indicated generally at 10". The support 10" of the third embodiment is similar to the support 10 of the first embodiment except as described hereinafter. Accordingly, like components are indicated by corresponding reference numerals followed by a double prime. The support 10" may comprise a base 18" for resting on a surface (not shown), and a pole assembly 20" configured for attachment to the base to suspend a medical bag (not shown) above the support surface. The pole assembly 20" may include padding 21". The base 18" may comprise a support portion 24" for supporting the support 10" on the support surface and an attachment portion 25" for attaching the pole assembly 20" to the base and movably attaching a medical device mounting assembly 14" to the base. The support portion 24" may be configured to engage the support surface. Feet 28" may be attached to a bottom of the support portion 24" for engaging the support surface to stabilize the support 10" on the support surface. In the illustrated embodiment, each foot 28" is pivotably attached to the bottom of the support portion 24" and movable between a deployed position (FIG. 25) and a stowed position (FIGS. 33 and 34). In the stowed position, the feet 28" may be received in pockets 30" in the bottom of the support portion 24" so that the feet are substantially within an outer perimeter of the support portion. In the deployed position the feet 28" may extend outward past the outer perimeter of the support portion 24" to provide a wider support base for the support 10". The feet 28" could be fixedly attached to the support portion 24" without departing from the scope of the disclosure. In the illustrated embodiment, there are four feet 28" attached to the support portion 24". However, any number of feet is envisioned.

The support portion 24" may have a top surface 34". Sides 36" of the support portion 24" may have cutouts 38". In the illustrated embodiment, there are two cutouts 38" in a front side 36" of the support 10", and one cutout 38" in each of the lateral sides 36" of the support. A portion of each cutout 38" may be aligned with at least a portion of a respective foot 28" when the foot is in the stowed position. The cutouts 38" provide access to the feet 28" from a side and/or from above the support portion 24" so that the feet can be grasped and moved to the deployed position when the support 10" is supported on a support surface. A tab 39" on a top of each foot 28" may provide structure to facilitate grasping the foot and moving it between the stowed position and the deployed position.

Referring to FIGS. 27-32, each foot 28" may include an anchor portion 40" that is pivotably attached to the bottom of the support portion 24" by a fastener 41". The anchor portion 40" may have an opening 42" (FIGS. 29 and 30) and a plurality of notches 43" formed in a top surface of the anchor portion 40" around the opening. A plurality of flanges 44" extend from a bottom surface of the anchor portion 40" partially across the opening 42". The flanges 44" may comprise discrete flexible members defining gaps 45" between adjacent flanges.

Detents 46" (FIG. 31) may be formed on a bottom surface of an associated pocket 30" in the support portion 24" of the base 18". A post 47" may extend from the bottom surface of the pocket 30" and ribs 48" may be formed on an outer surface of the post 47". The post 47" is received in the opening 42" in the foot 28" and the foot is secured to the support portion 24" by the fastener 41". The detents 46" in the pocket 30" may be configured to be removably received in the notches 43" on the foot 28", and the ribs 48" on the post 47" may be configured to engage a surface extending around the opening 42" to releasably hold the foot in any of several positions with respect to the support portion 24". Pivoting the foot 28" causes the notches 43" on the foot to move relative to the detents 46". For the notches 43" to clear the detents 46" during rotation of the foot 28", the anchor portion 40" of the foot must move away from the support portion 24" to provide the necessary clearance. The angled surfaces on the notches 43" and detents" urge the foot 28" away from the support portion 24" when a rotational force is applied to the foot. To allow for this separation, the flanges 44" on the foot 28" engage a washer 49" of the fastener 41" and flex upward allowing the notches 43" to slide down the detents 46" to at least partially disengage from the detents (FIG. 32). Once the notches 43" clear the detents 46", the foot 28" can be rotated to a desired position. After rotating the foot 28" to the desired position, the foot is released and the flanges 44" will urge the notches 43" back into engagement with the detents 46" and hold the foot in the new position. It will be understood that the engagement between the detents 46" and notches 43", the engagement between the ribs 48" and the surface around the opening 42", and the engagement between the flanges 44" and the washer 49" hold the foot 28" in both the fully stowed and fully deployed positions.

Referring to FIGS. 25 and 35-37, the attachment portion 25" of the base 18" may comprise an attachment member 46" and the attachment portion may be formed integrally with the support portion 24". The attachment portion 25" may be disposed generally at the back of the support portion 24" and may extend upward from the support portion. The attachment member 46" may be fixedly attached to a remainder of the attachment portion 25". In the illustrated embodiment, the attachment member 46" is formed as one piece with the remainder of the attachment portion 25". The attachment member 46" can be formed in other ways without departing from the scope of the disclosure.

The attachment member 46" may pivotally attach a mounting portion 50" of the medical device mounting assembly 14" to the attachment portion 25" of the base 18". The attachment member 46" may comprise a tab 52" projecting from an arcuate section 54" of the attachment portion 25". The tab 52" may include a pivot hole 56" generally at a front end of the tab and a plurality of locking holes 58" arcuately spaced from one another and extending generally along a back end of the tab adjacent the arcuate section 54" of the attachment portion 25". The locking holes 58" are arranged at an approximately constant distance from the pivot hole 56". The locking holes 58" may be arranged to provide about 45 degrees of pivot adjustment between the mounting portion 50" and the attachment member 46" about a pitch axis extending through the pivot hole 56". In the illustrated embodiment, the pivot hole 56" is disposed at a top of the front end of the tab 52", and a topmost locking hole 58" is disposed near a top of the back end of the tab. It is envisioned that the attachment member 46" may have other shapes and the pivot hole 56" and locking holes 58" may be disposed in other locations.

Figure 26:
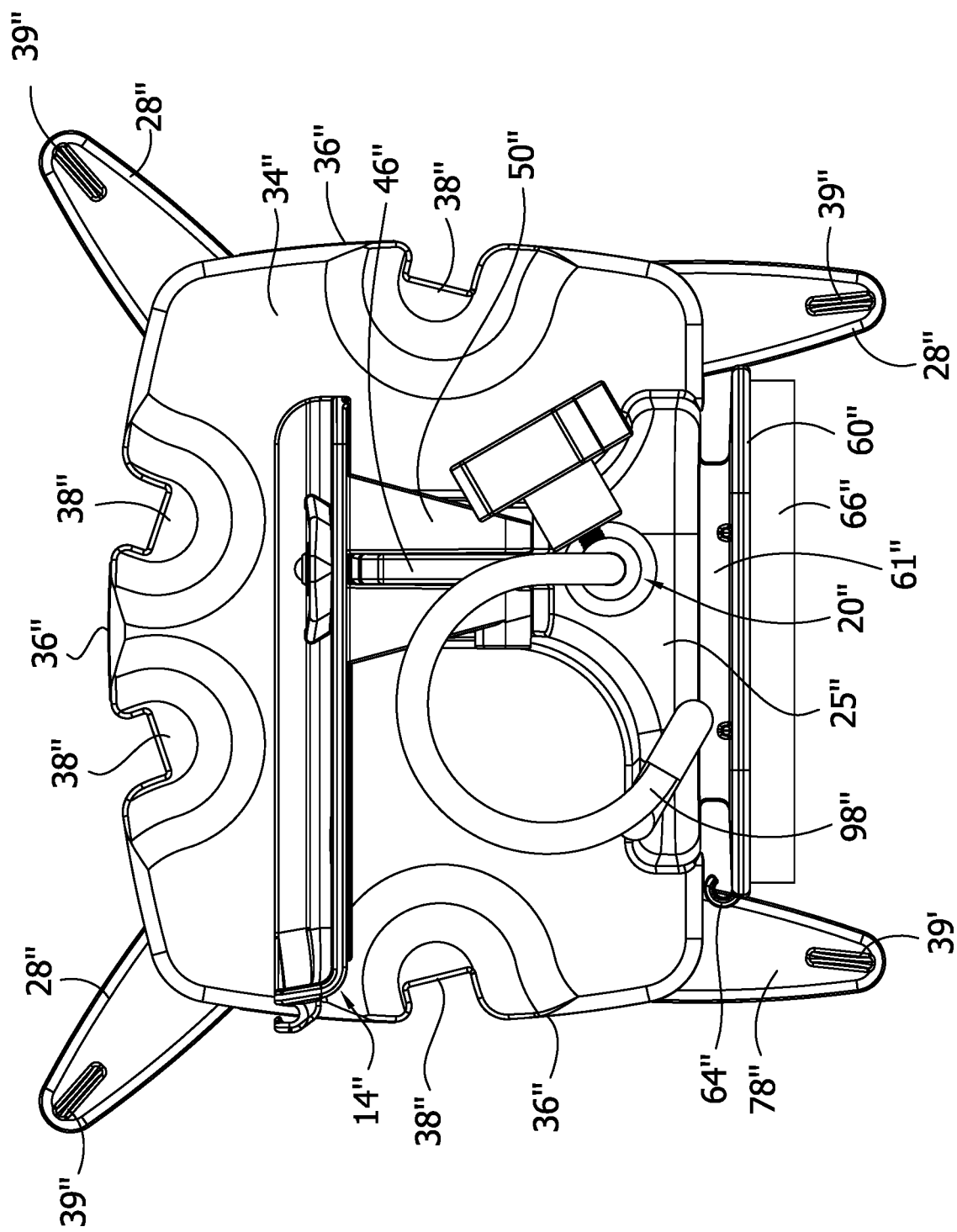
FIG. 26 is a top view of the support of FIG. 25.
Figure 27:
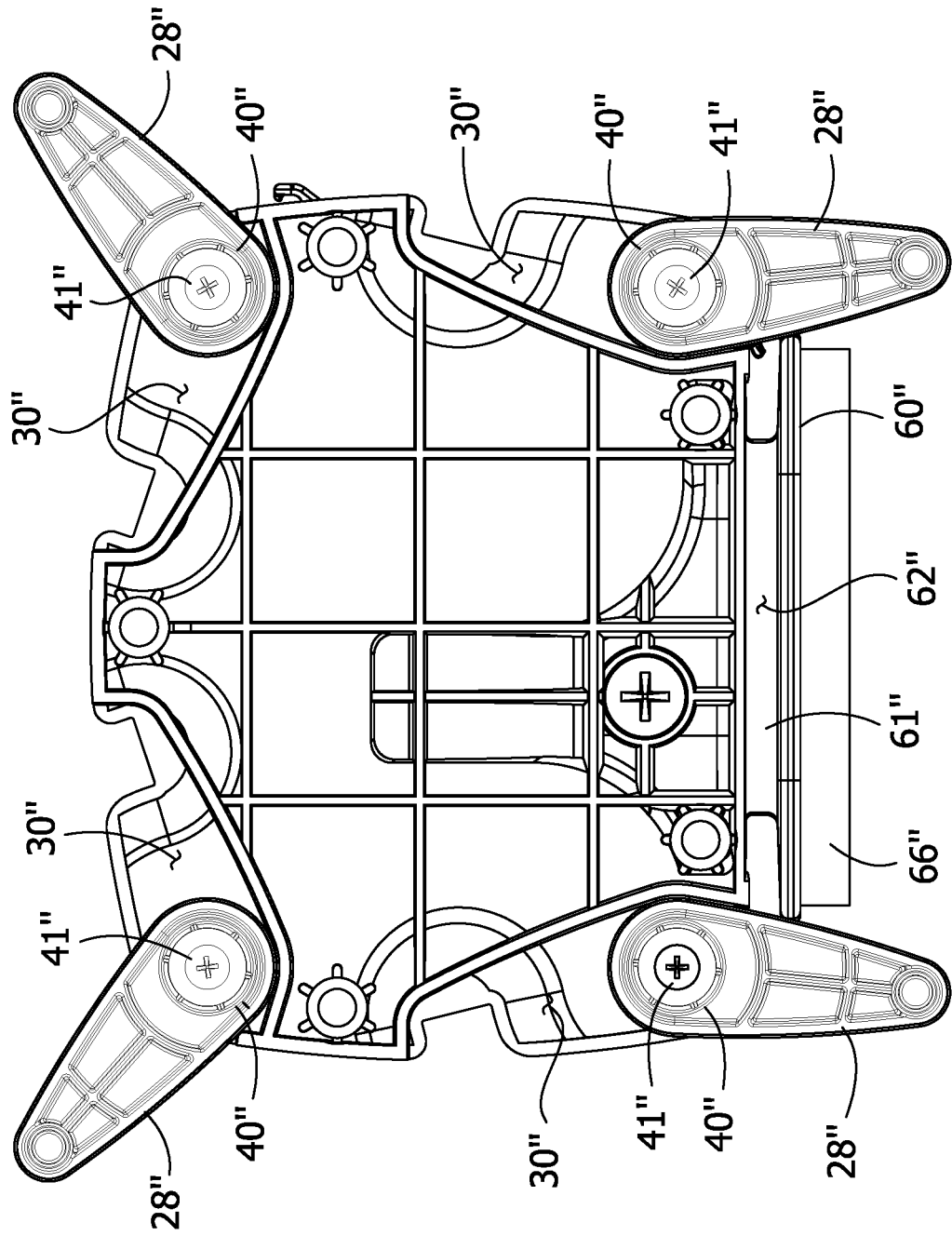
FIG. 27 is a bottom view of the support of FIG. 25.
Figure 28:
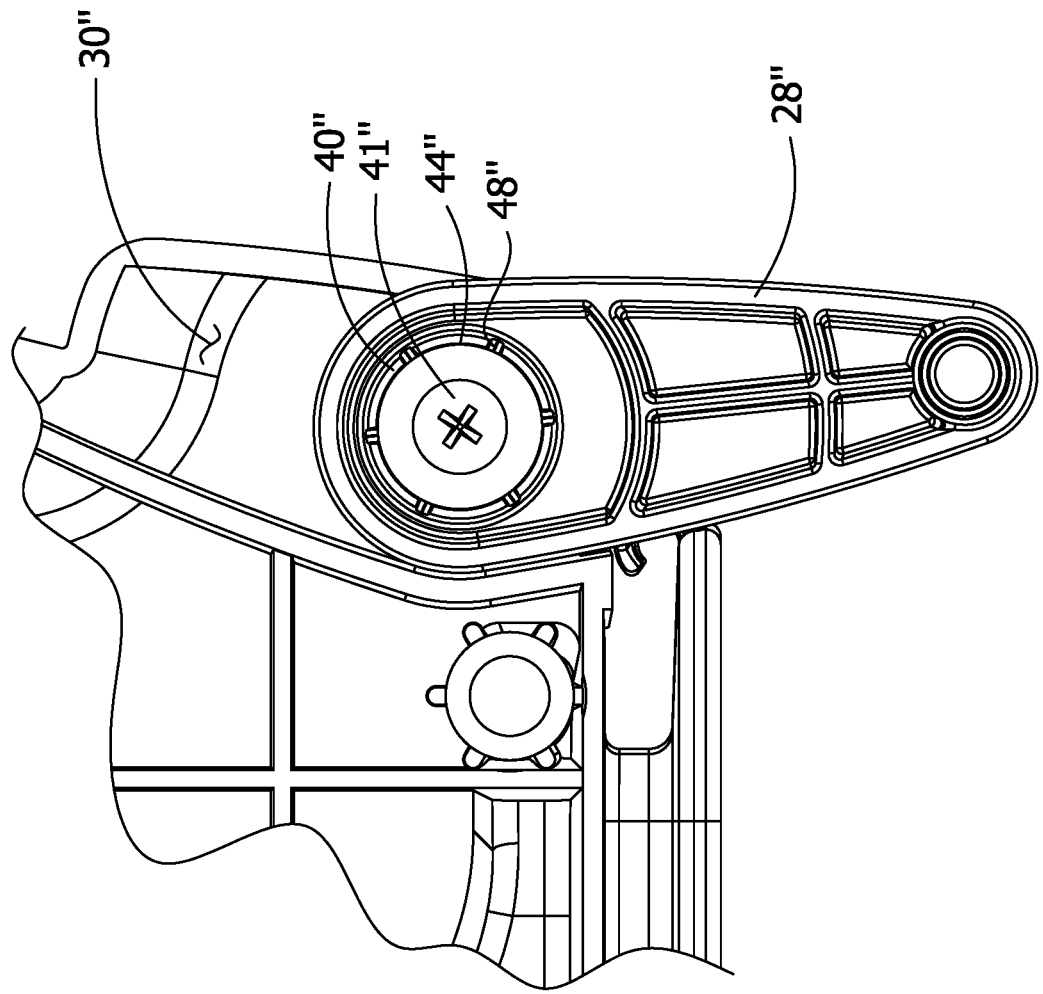
FIG. 28 is an enlarged fragmentary view of the support shown in FIG. 27.
Figure 29:
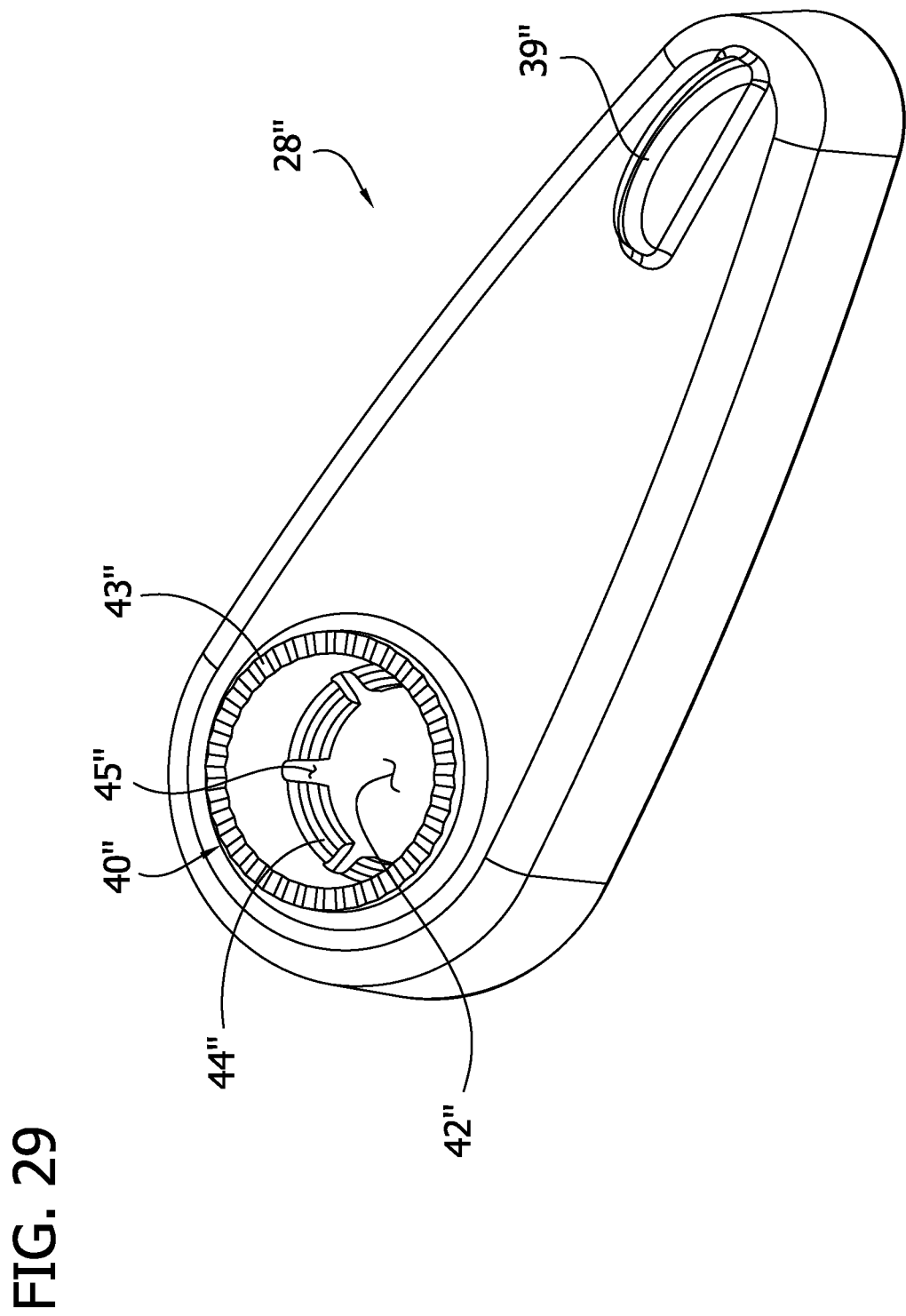
FIG. 29 is a top perspective of a foot of the support of FIG. 25.
Figure 30:
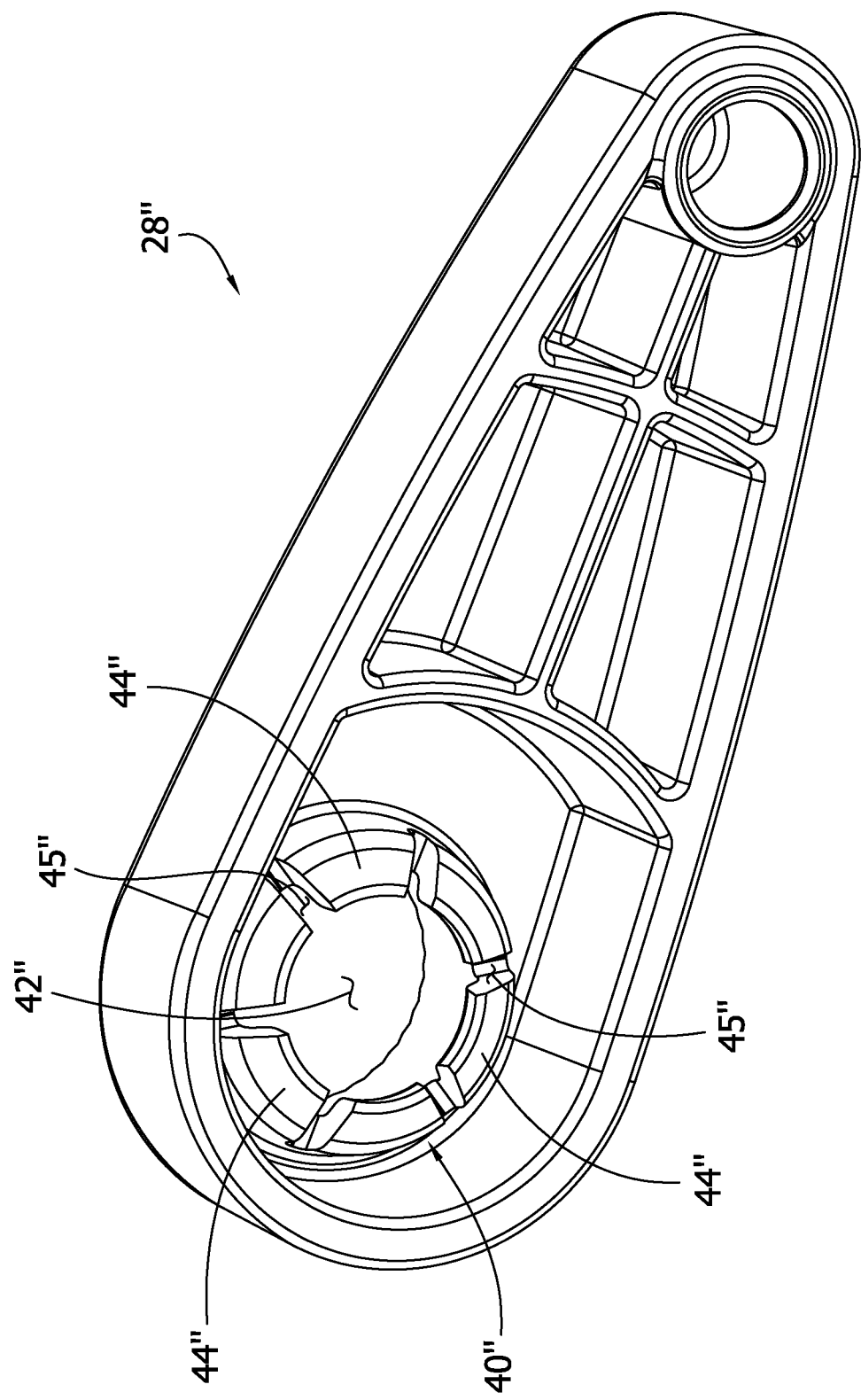
FIG. 30 is a bottom perspective of the foot of the support of FIG. 25.
Figure 31:
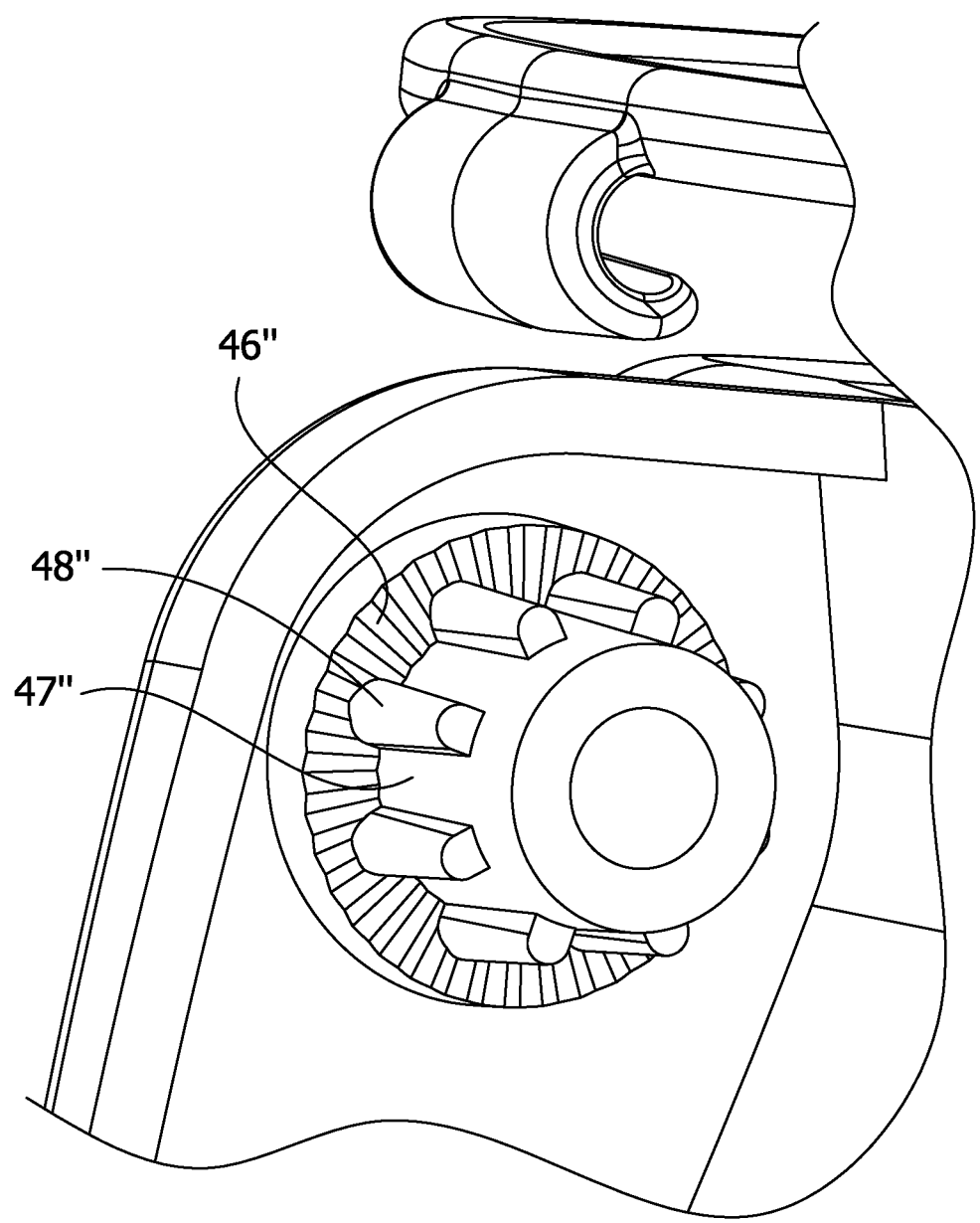
FIG. 31 is an enlarged fragmentary perspective of the support of FIG. 27 with a foot removed.
Figure 36:
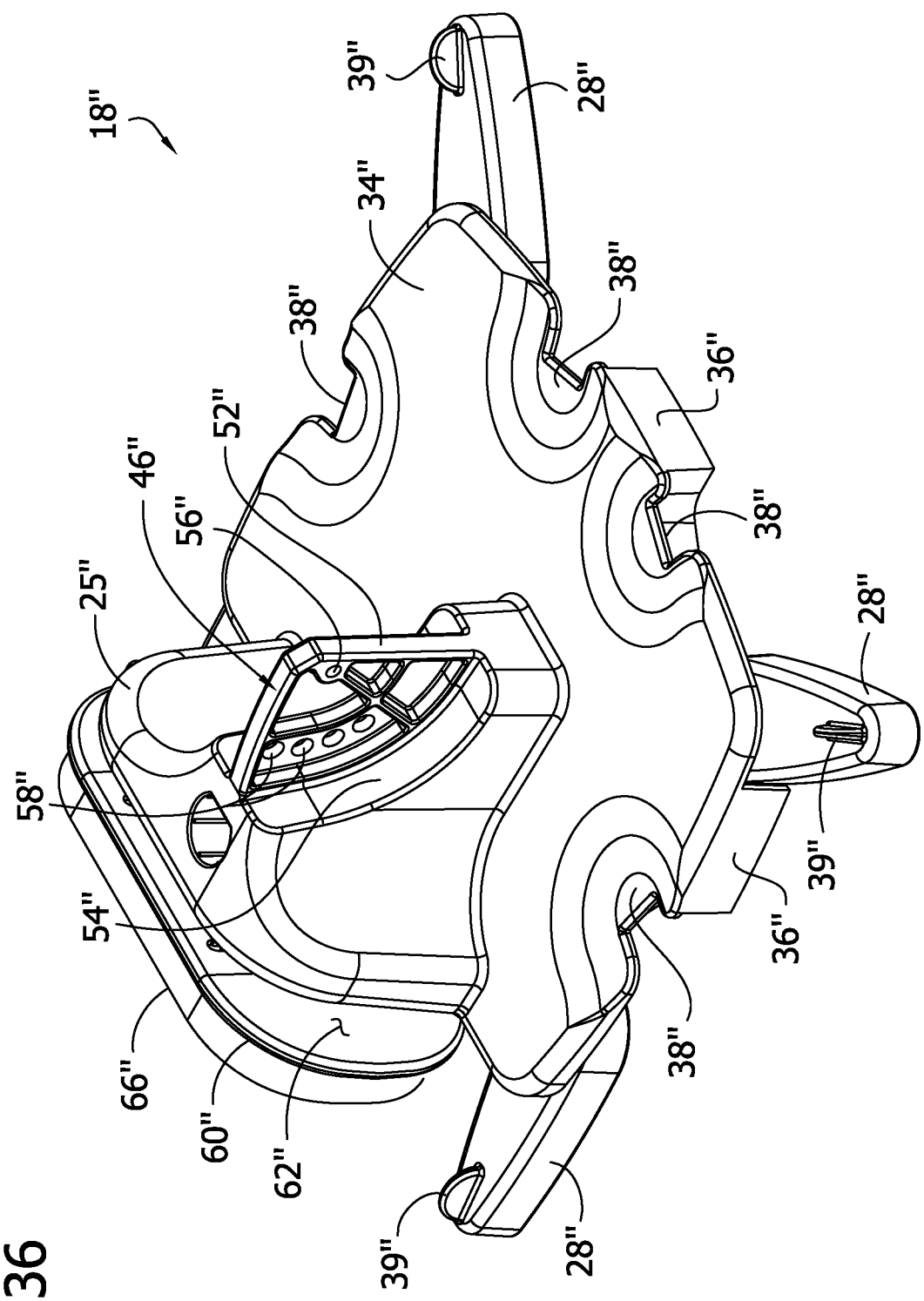
FIG. 36 is a front perspective of a base of the support of FIG. 35.
Figure 37:
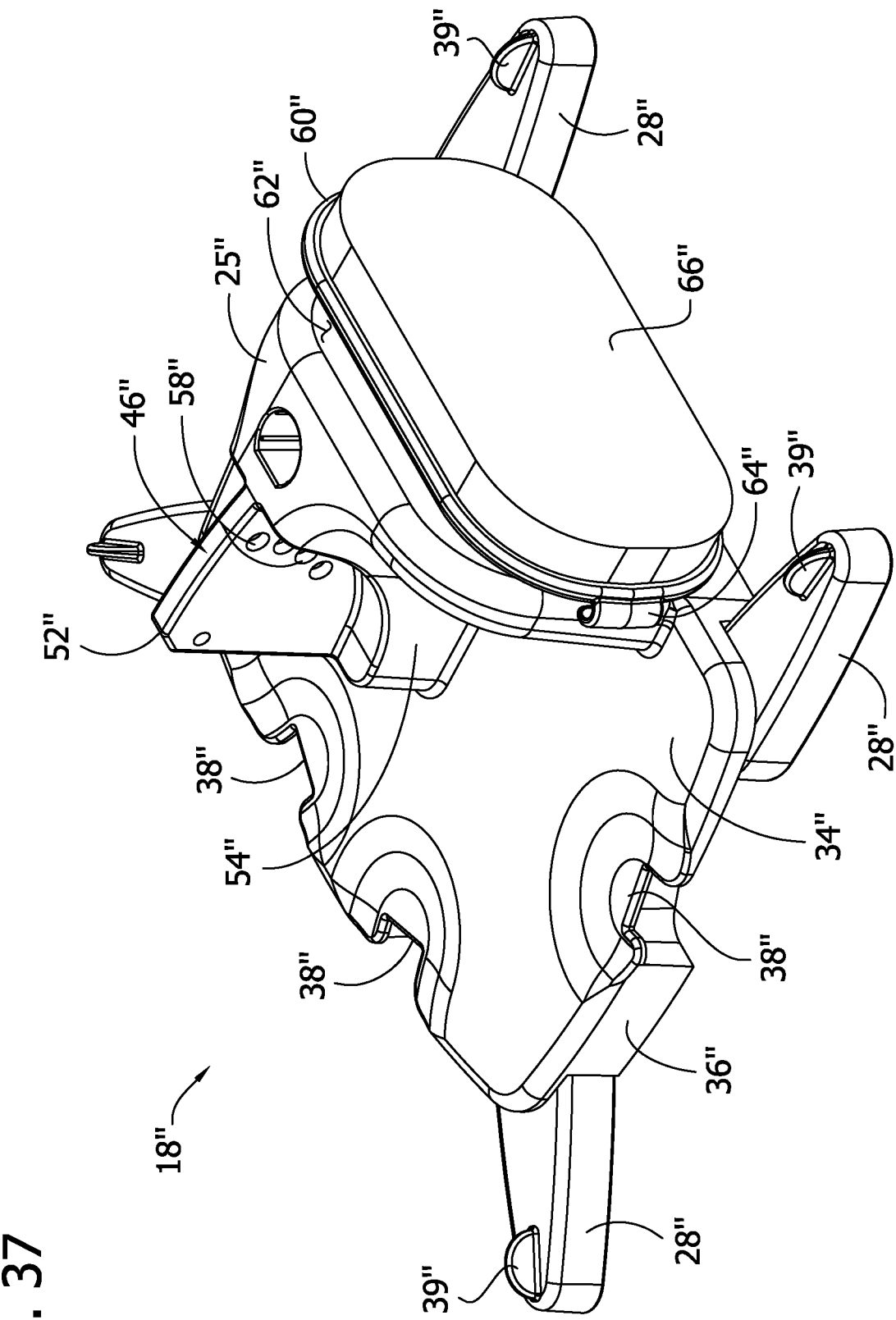
FIG. 37 is a rear perspective of the base of the support of FIG. 35.

Referring to FIGS. 36 and 37, the attachment portion 25" further comprises a spacer 60" mounted at a back of the attachment portion by an extension portion 61" (FIG. 26). An annular gap 62" extending around the extension potion 61" is formed between the flange portion 60" and the arcuate section 54". The gap 62" may hold any excess medical tubing in a wrapped configuration. A tube holder 64" may be disposed on the flange portion 60" to retain a portion of the medical tubing. The gap 62" and tube holder 64" may individually or collectively be considered a tube holder. A padding 66" may be attached to the spacer 60". The function of the spacer 60" including the padding 66" will be explained below.

Figure 38:
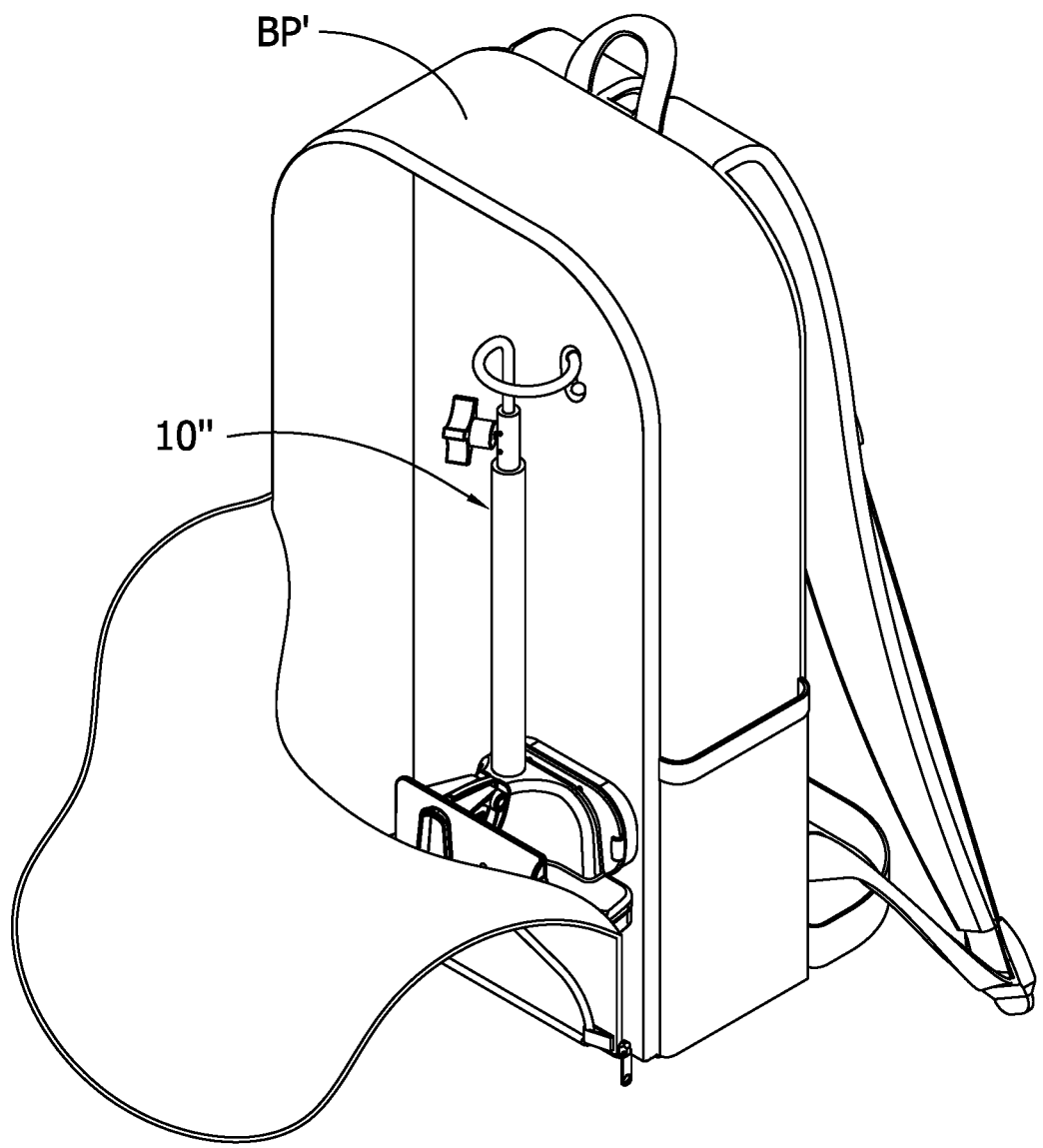
FIG. 38 is a perspective of the support of FIG. 25 shown inside a backpack.

Referring to FIG. 38, the support 10" may be carried in a backpack BP within an internal compartment thereof such that a medical bag 12" is suspended by the support inside the backpack. The feet 28" of the support 10" may be moved to the stowed position (FIG. 33) and the support inserted into the backpack BP. However, the feet 28" may be moved to the deployed position (FIG. 25) to facilitate inserting the support into the backpack BP without departing from the scope of the disclosure. The backpack BP allows the patient the freedom to be mobile while using the support 10" and pump 16" mounted on the support. The same support 10" can be used for table top support out of the backpack BP by moving the feet 28" to the deployed position for stability. The spacer 60", and in particular the padding 66" is positioned to engage the back of the wearer. The contact holds off the base 18" of the support 10", thereby providing space between the wearer's back and the pole 20". Thus, the bag of nutrients will not be likely to be compressed against the wearer's back which could detrimentally affect operation of the feeding system. Additionally, the padding 66" provides a soft surface for engaging the wearer making the assembly more comfortable to wear.

When introducing elements of the present invention or the preferred embodiment(s) thereof, the articles "a," "an," "the," and "said" are intended to mean that there are one or more of the elements. The terms "comprising," "including," and "having" are intended to be inclusive and mean that there may be additional elements other than the listed elements.

In view of the above, it will be seen that the several objects of the invention are achieved and other advantageous results attained.

As various changes could be made in the above construction without departing from the scope of the invention, it is intended that all matter contained in the above description or shown in the accompanying drawings shall be interpreted as illustrative and not in a limiting sense. It is understood that any of the particular embodiments of the present invention may include one or more of the aspects or features of the invention as described herein and illustrated in the drawings.

What is claimed is:

1. A combination backpack and medical fluid bag support, comprising:
   a medical fluid bag support comprising a base assembly having at least one selectively adjustable foot, the base assembly configured to engage a medical device, a pole assembly coupled to the base assembly, the pole assembly having a medical fluid bag attachment portion configured to support the feeding bag thereunto and configured to dispose the medical fluid bag attachment portion at at least one predetermined head height above the base assembly, the medical fluid bag attachment portion comprising a tube member including a curved section; and
   a backpack portion configured to be supported on a wearer's shoulder and defining an internal storage compartment sized to receive therein the medical fluid bag support,
   the curved section of the medical fluid bag attachment portion being spaced away from the rest of the pole assembly such that the medical fluid bag attachment portion is configured to support the feeding bag to deliver medical fluid to a patient when the medical fluid bag support is received in the backpack portion;
   wherein the base assembly has a plurality of independently adjustable feet, each of the independently adjustable feet having a stowed position and a plurality of selectively lockable deployed positions, and wherein the internal storage compartment is sized to receive therein the medical fluid support when each of the independently adjustable feet is in the stowed position.

2. The combination backpack and medical fluid bag support of claim 1, wherein the at least one predetermined head height includes a first predetermined head height selectable when the medical fluid bag support is disposed in the internal storage compartment, and a second predetermined head height selectable when the at least one selectively adjustable foot is engaged with a surface.

3. The combination backpack and medical fluid bag support of claim 1, wherein each of the plurality of independently adjustable feet is pivotable between the deployed positions and the stowed position.

4. The combination backpack and medical fluid bag support of claim 1, wherein the pole assembly comprises a first elongate member and a second elongate member telescopingly received in the first elongate member.

5. The combination backpack and medical fluid bag support of claim 4, wherein the second elongate member comprises a first straight section for receipt in the first elongate member and a second curved section extending from the first straight section for attaching the medical bag.

6. The combination backpack and medical fluid bag support of claim 5, further comprising a lock for securing the second elongate member at at least one of a plurality of preselected positions relative to the first elongate member.

7. The combination backpack and medical fluid bag support of claim 4, wherein the attachment portion and the second elongate member are formed as one piece of material.

8. The combination backpack and medical fluid bag support of claim 1, further comprising a medical device mounting assembly secured to the base assembly.

9. The combination backpack and medical fluid bag support of claim 1, the base assembly having a first configuration for supporting the medical bag on a surface and a second configuration for supporting the medical bag in the backpack.

10. The combination backpack and medical fluid bag support of claim 1 wherein the curved section lies in a plane perpendicular to a longitudinal axis of the pole assembly.

11. A medical fluid bag support system, comprising:
    a base assembly comprising:
    a support portion for supporting the support system on a surface; and
    an attachment portion;
    a medical device mounting assembly pivotably attached to the attachment portion by releasable locking components on the medical device mounting assembly and attachment portion, and configured to secure a medical device to the base assembly, the releasable locking components adjusting the position of the medical device with respect to the attachment portion by releasably locking the medical device mounting assembly in multiple positions relative to the attachment portion; and
    a pole assembly comprising a medical bag attachment portion for attaching a medical bag to the pole assembly, the pole assembly being mountable on the base assembly such that when the pole assembly is mounted on the base assembly and the base assembly is on the surface, the medical bag attachment portion is disposed above the base suspending the medical bag above the surface
    wherein the medical device mounting assembly is configured to pivot relative to the pole assembly;
    wherein the support portion and the attachment portion are formed as one piece of material.

12. The medical fluid bag support system of claim 11, in combination with a backpack, the base assembly having a first configuration for supporting the medical bag on the surface and a second configuration for supporting the medical bag in the backpack.

13. The combination backpack and medical fluid bag support system of claim 12 further comprising padding disposed at a back of the base assembly for engaging a wearer of the backpack when the support system is in the backpack.

* * * * *